(12) United States Patent
Shioda et al.

(10) Patent No.: US 11,203,590 B2
(45) Date of Patent: Dec. 21, 2021

(54) HETEROCYCLIC COMPOUND AND HARMFUL-ARTHROPOD CONTROL AGENT CONTAINING SAME

(71) Applicant: Sumitomo Chemical Company, Limited, Tokyo (JP)

(72) Inventors: Takayuki Shioda, Takarazuka (JP); Daisuke Oohira, Takarazuka (JP); Kaori Ikari, Takarazuka (JP); Natsuru Hiraguri, Osaka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 205 days.

(21) Appl. No.: 16/630,078

(22) PCT Filed: Jul. 12, 2018

(86) PCT No.: PCT/JP2018/026289
§ 371 (c)(1),
(2) Date: Jan. 10, 2020

(87) PCT Pub. No.: WO2019/013273
PCT Pub. Date: Jan. 17, 2019

(65) Prior Publication Data
US 2020/0165244 A1 May 28, 2020

(30) Foreign Application Priority Data
Jul. 13, 2017 (JP) .............................. JP2017-136943

(51) Int. Cl.
*C07D 471/04* (2006.01)
*A01N 43/90* (2006.01)
*C07D 401/12* (2006.01)
*C07D 401/14* (2006.01)

(52) U.S. Cl.
CPC ........... *C07D 471/04* (2013.01); *A01N 43/90* (2013.01); *C07D 401/12* (2013.01); *C07D 401/14* (2013.01)

(58) Field of Classification Search
CPC .. C07D 471/04; C07D 401/12; C07D 401/14; A01N 43/90
See application file for complete search history.

(56) References Cited

U.S. PATENT DOCUMENTS

| | | | |
|---|---|---|---|
| 9,668,482 B1 * | 6/2017 | Tanabe | A01N 43/90 |
| 2015/0246911 A1 * | 9/2015 | Takahashi | C07D 471/04 |
| | | | 514/302 |
| 2016/0368915 A1 | 12/2016 | Tanabe et al. | |
| 2017/0135348 A1 | 5/2017 | Tanabe et al. | |
| 2018/0271099 A1 | 9/2018 | Fischer et al. | |
| 2018/0303097 A1 | 10/2018 | Wilcke et al. | |
| 2019/0150447 A1 | 5/2019 | Oohira et al. | |
| 2019/0359588 A1 | 11/2019 | Sakanishi et al. | |
| 2020/0323212 A1 * | 10/2020 | Okuda | A01N 43/90 |

(Continued)

FOREIGN PATENT DOCUMENTS

| CN | 103717598 A | 4/2014 |
|---|---|---|
| CN | 105358555 A | 2/2016 |

(Continued)

OTHER PUBLICATIONS

Office Action dated Jun. 29, 2021 in CN Application No. 201880045983.7.
International Preliminary Report on Patentability dated Jan. 14, 2020 in International Application No. PCT/JP2018/026289.
International Search Report dated Aug. 28, 2018 in International Application No. PCT/JP2018/026289.

(Continued)

*Primary Examiner* — Alexander R Pagano
(74) *Attorney, Agent, or Firm* — Panitch Schwarze Belisario & Nadel LLP

(57) ABSTRACT

A compound represented by formula (I), which is highly effective in controlling harmful arthropods, an intermediate thereof and a production method thereof are described. In formula (I), $A^1$ represents CH or a nitrogen atom; $R^1$ represents a C1-C6 alkyl group optionally having one or more halogen atoms; $R^5$ represents $CF_3$, $C_2F_5$, or $S(O)_mCF_3$; Q represents $NR^2C(O)OR^3$ or $N=CR^4R^6$; $R^2$ represents a hydrogen atom or the like; $R^3$ represents a C1-C6 alkyl group optionally having one or more halogen atoms or the like; $R^4$ represents a hydrogen atom or the like; $R^6$ represents a phenyl group optionally having one or more substituents selected from group D, or the like; and n and m each independently are 0, 1, or 2. Group D: a group consisting of C1-C6 alkyl groups optionally having one or more halogen atoms and C1-C6 alkoxy groups optionally having one or more halogen atoms or the like.

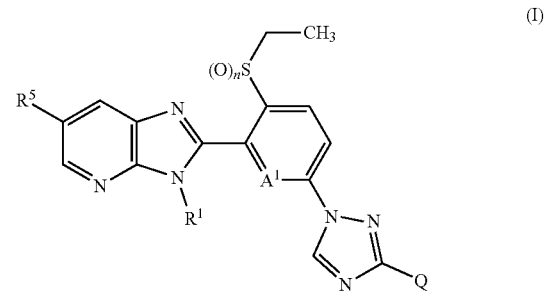

7 Claims, No Drawings

(56) References Cited

U.S. PATENT DOCUMENTS

2021/0059255 A1* 3/2021 Tanaka ................ C07D 487/04
2021/0070753 A1* 3/2021 Shioda .................. A01N 43/90
2021/0084903 A1* 3/2021 Orimoto ............. C07D 487/04

FOREIGN PATENT DOCUMENTS

| | | | |
|---|---|---|---|
| CN | 106103433 | A | 11/2016 |
| EP | 3115363 | A1 | 1/2017 |
| EP | 3348554 | A1 | 7/2018 |
| JP | 2016102104 | A | 6/2016 |
| JP | 2017052702 | A | 3/2017 |
| WO | 2013018928 | A1 | 2/2013 |
| WO | 2015002211 | A1 | 1/2015 |
| WO | 2015133603 | A1 | 9/2015 |
| WO | 2017025419 | A2 | 2/2017 |
| WO | 2017043341 | A1 | 3/2017 |
| WO | 2017043342 | A1 | 3/2017 |
| WO | 2017043385 | A1 | 3/2017 |
| WO | 2017043386 | A1 | 3/2017 |
| WO | 2017055185 | A1 | 4/2017 |
| WO | 2017082132 | A1 | 5/2017 |
| WO | 2018116945 | A1 | 6/2018 |

Extended European Search Report dated Feb. 24, 2021 in European Application No. 18831154.2.
Examination Report dated Aug. 9, 2021 in IN Application No. 202047004767.

* cited by examiner

HETEROCYCLIC COMPOUND AND HARMFUL-ARTHROPOD CONTROL AGENT CONTAINING SAME

CROSS-REFERENCE TO RELATED APPLICATION

This application is a Section 371 of International Application No. PCT/JP2018/026289, filed Jul. 12, 2018, which was published in the Japanese language on Jan. 17, 2019, under International Publication No. WO 2019/013273 A1, which claims priority under 35 U.S.C. 119(b) to Japanese Application No. 2017-136943 filed on Jul. 13, 2017, the disclosures of which are incorporated herein by reference in their entireties.

TECHNICAL FIELD

This patent application claims priority to and the benefit of Japanese Patent Application No. 2017-136943 filed on Jul. 13, 2017, the entire contents of which are incorporated herein by reference.

The present invention relates to a certain type of heterocyclic compound and a harmful-arthropod control agent containing the same.

BACKGROUND ART

To date, for the purpose of controlling harmful arthropods, various compounds have been studied and come into practical use.

Also, a certain class of compound has been known to have an effect on controlling pests (see, for example, Patent Document 1).

CITATION LIST

Patent Document

Patent Document 1: WO 2017/025419 A1

SUMMARY OF THE INVENTION

Problems to be Solved by Invention

An object of the present invention is to provide a compound having an excellent efficacy for controlling harmful arthropods.

Means to Solve Problems

The present inventors have intensively studied to find compounds having an excellent efficacy for controlling harmful arthropods, and as a result, found that a compound represented by the following formula (I) has an excellent efficacy for controlling harmful arthropods.

That is, the present invention is as follows.

[1] A compound represented by formula (I):

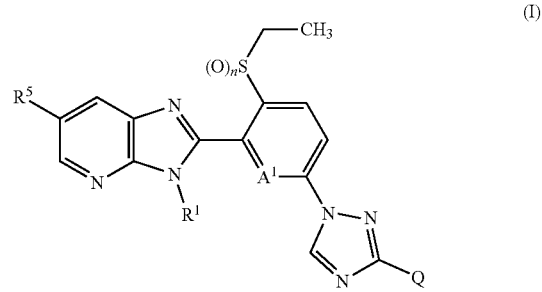

[wherein:
$A^1$ represents CH or a nitrogen atom;
$R^4$ represents a C1-C6 alkyl group optionally having one or more halogen atoms;
$R^5$ represents $CF_3$, $C_2F_5$, or $S(O)_mCF_3$;
Q represents $NR^2C(O)OR^3$ or $N=CR^4R^6$;
$R^2$ represents a C1-C6 alkyl group optionally having one or more halogen atoms, a C3-C6 cycloalkyl group optionally having one or more halogen atoms, $C(O)OR^3$ or a hydrogen atom;
$R^3$ represents a C1-C6 alkyl group optionally having one or more halogen atoms, a phenyl group optionally having one or more substituents selected from Group D, or a benzyl group optionally having one or more substituents selected from Group D;
$R^4$ represents a C1-C6 alkyl group optionally having one or more halogen atoms, a phenyl group optionally having one or more substituents selected from Group D, or a hydrogen atom;
$R^6$ represents a C1-C6 alkyl group optionally having one or more halogen atoms, a phenyl group optionally having one or more substituents selected from Group D, or $NR^7R^6$;
$R^4$ and $R^6$ may combine together with a carbon atom to which $R^4$ and $R^6$ are attached to form a C3-C8 cycloalkylidene group;
$R^7$, $R^8$, $R^9$ and $R^{10}$ are identical to or different from each other and each represents independently a C1-C6 alkyl group optionally having one or more halogen atoms;
n is 0, 1, or 2; and
m is 0, 1, or 2,
Group D: a group consisting of a C1-C6 alkyl group optionally having one or more halogen atoms, a C1-C6 alkoxy group optionally having one or more halogen atoms, a C1-C6 alkylsulfonyl group optionally having one or more halogen atoms, a nitro group, a cyano group, $NR^9R^{10}$ and a halogen atom] (hereinafter, referred to as "Present compound" or "Compound of the present invention").
[2] The compound according to [1], wherein:
$R^1$ represents a methyl group; and $A^1$ represents a nitrogen atom.
[3] A composition for controlling a harmful arthropod comprising the compound according to [1] or [2] and an inert carrier.
[4] A method for controlling a harmful arthropod comprising applying an effective amount of the compound according to [1] or [2] to the harmful arthropod or a habitat where a harmful arthropod lives.

[5] A compound represented by formula (II):

(II)

[wherein:
$A^1$ represents CH or a nitrogen atom;
$R^1$ represents a C1-C6 alkyl group optionally having one or more halogen atoms;
$R^5$ represents $CF_3$, $C_2F_5$, or $S(O)_mCF_3$;
Q represents $NR^2C(O)OR^3$ or $N=CR^4R^6$;
$R^2$ represents a C1-C6 alkyl group optionally having one or more halogen atoms, a C3-C6 cycloalkyl group optionally having one or more halogen atoms, $C(O)OR^3$ or a hydrogen atom;
$R^3$ represents a C1-C6 alkyl group optionally having one or more halogen atoms, a phenyl group optionally having one or more substituents selected from Group D, or a benzyl group optionally having one or more substituents selected from Group D;
$R^4$ represents a C1-C6 alkyl group optionally having one or more halogen atoms, a phenyl group optionally having one or more substituents selected from Group D, or a hydrogen atom;
$R^6$ represents a C1-C6 alkyl group optionally having one or more halogen atoms, a phenyl group optionally having one or more substituents selected from Group D, or $NR^7R^8$;
$R^4$ and $R^6$ may combine together with a carbon atom to which $R^4$ and $R^6$ are attached to form a C3-C8 cycloalkylidene group;
$R^7$, $R^8$, $R^9$ and $R^{10}$ are identical to or different from each other and each represents independently a C1-C6 alkyl group optionally having one or more halogen atoms;
n is 0, 1, or 2; and
m is 0, 1, or 2,
Group D: a group consisting of a C1-C6 alkyl group optionally having one or more halogen atoms, a C1-C6 alkoxy group optionally having one or more halogen atoms, a C1-C6 alkylsulfonyl group optionally having one or more halogen atoms, a nitro group, a cyano group, $NR^9R^{10}$ and a halogen atom]
(hereinafter, referred to as "Present intermediate compound" or "Intermediate of the present invention").
[6] A method for preparing the compound represented by formula (I) according to [1] comprising:
a step of reacting a compound represented by formula (M1):

(M1)

[wherein:
X represents a halogen atom;
$A^1$ represents CH or a nitrogen atom;
$R^1$ represents a C1-C6 alkyl group optionally having one or more halogen atoms;
$R^5$ represents $CF_3$, $O_2F_5$, or $S(O)_mCF_3$;
n is 0, 1, or 2; and
m is 0, 1, or 2]
with a compound represented by formula (M2):

(M2)

[wherein:
Q represents $NR^2C(O)OR^3$ or $N=CR^4R^6$;
$R^2$ represents a C1-C6 alkyl group optionally having one or more halogen atoms, a C3-C6 cycloalkyl group optionally having one or more halogen atoms, $C(O)OR^3$ or a hydrogen atom;
$R^3$ represents a C1-C6 alkyl group optionally having one or more halogen atoms, a phenyl group optionally having one or more substituents selected from Group D, or a benzyl group optionally having one or more substituents selected from Group D;
$R^4$ represents a C1-C6 alkyl group optionally having one or more halogen atoms, a phenyl group optionally having one or more substituents selected from Group D, or a hydrogen atom;
$R^6$ represents a C1-C6 alkyl group optionally having one or more halogen atoms, a phenyl group optionally having one or more substituents selected from Group D, or $NR^7R^8$;
$R^4$ and $R^6$ may combine together with a carbon atom to which $R^4$ and $R^6$ are attached to form a C3-C8 cycloalkylidene group; and
$R^7$, $R^8$, $R^9$ and $R^{10}$ are identical to or different from each other and each represents independently a C1-C6 alkyl group optionally having one or more halogen atoms,
Group D: a group consisting of a C1-C6 alkyl group optionally having one or more halogen atoms, a C1-C6 alkoxy group optionally having one or more halogen atoms, a C1-C6 alkylsulfonyl group optionally having one or more halogen atoms, a nitro group, a cyano group, $NR^9R^{10}$ and a halogen atom]
in the presence of a base.
[7] A method for preparing the compound represented by formula (I) according to [1] comprising:
a step of reacting the compound represented by formula (II) according to [5] in the presence of an acid.

Effect of Invention

The present invention can control a harmful arthropod. The present invention can also prepare the compound represented by formula (I).

MODE FOR CARRYING OUT THE INVENTION

The substituent(s) as described herein is/are explained below.
The term "halogen atom" refers to a fluorine atom, a chlorine atom, a bromine atom, or an iodine atom.

When the substituents have two or more halogen atoms, these halogen atoms may be identical to or different from each other.

The expression "CX-CY" as used herein represents that the number of carbon atom is from X to Y. For example, the expression "C1-C6" represents that the number of carbon atom is from 1 to 6.

Examples of "alkyl group" include methyl group, ethyl group, propyl group, isopropyl group, 1,1-dimethylpropyl group, 1,2-dimethylpropyl group, 1-ethylpropyl group, butyl group, sec-butyl group, tert-butyl group, pentyl group and hexyl group.

The "cycloalkyl group" refers to cyclopropyl group, cyclobutyl group, cyclopentyl group, and cyclohexyl group.

Examples of "cycloalkylidene group" include cyclopropylidene group, cyclobutylidene group, cyclopentylidene group, cyclohexylidene group, cyclopentylidene group, and cyclooctylidene group.

Examples of "alkoxy group" include methoxy group, ethoxy group, propoxy group, butoxy group, pentoxy group, and hexyloxy group.

Examples of "alkylsulfonyl group" include methylsulfonyl group, ethylsulfonyl group, propylsulfonyl group, isopropylsulfonyl group, etc.

Examples of "C1-C6 alkyl group optionally having one or more halogen atoms" include perfluoroalkyl group, specifically trifluoromethyl group, pentafluoroethyl group, etc.

Examples of "C1-C6 alkoxy group optionally having one or more halogen atoms" include perfluoroalkyloxy group, specifically trifluoromethyloxy group, pentafluoroethyloxy group, etc.

Examples of "C1-C6 alkylsulfonyl group optionally having one or more halogen atoms" include perfluoroalkylsulfonyl group, specifically trifluoromethylsulfonyl group, pentafluoroethylsulfonyl group, etc.

Examples of "phenyl group optionally having one or more substituents selected from Group D" include phenyl group, methoxyphenyl group, nitrophenyl group, chlorophenyl group, nitrophenyl group, cyanophenyl group, and trifluoromethylphenyl group, etc., specifically 4-methoxyphenyl group, 4-nitrophenyl group, 4-chlorophenyl group, 4-nitrophenyl group, 4-cyanophenyl group, and 4-trifluoromethylphenyl group, etc.

Examples of "benzyl group optionally having one or more substituents selected from Group D" include benzyl group, phenyl group, methoxybenzyl group, nitrobenzyl group, chlorobenzyl group, nitrobenzyl group, cyanobenzyl group, and trifluoromethylbenzyl group, etc., specifically 4-methoxybenzyl group, 4-nitrobenzyl group, 4-chlorobenzyl group, 4-nitrobenzyl group, 4-cyanobenzyl group, and 4-trifluoromethylbenzyl group, etc.

Examples of the embodiment of the compound of the present invention include the following compounds.

Embodiment 1

A compound of the present invention, wherein $R^1$ represents a C1-C6 alkyl group.

Embodiment 2

The compound according to Embodiment 1, wherein $R^2$ represents a C1-C6 alkyl group, $C(O)OR^3$ or a hydrogen atom; $R^3$ represents a C1-C6 alkyl group; $R^4$ represents a C1-C6 alkyl group or a hydrogen atom; $R^6$ represents a C1-C6 alkyl group, a phenyl group optionally having one or more substituents selected from Group D, or $NR^7R^8$; and $R^7$ and $R^8$ are identical to or different from each other and each represents independently a C1-C6 alkyl group.

Embodiment 3

The compound according to Embodiment 1, wherein $R^2$ represents a C1-C6 alkyl group, $C(O)OR^3$ or a hydrogen atom; $R^3$ represents a C1-C6 alkyl group; $R^4$ represents a hydrogen atom; and $R^6$ represents a phenyl group optionally having one or more substituents selected from Group D.

Embodiment 4

The compound according to Embodiment 1, wherein $R^2$ represents a C1-C6 alkyl group, $C(O)OR^3$ or a hydrogen atom; $R^3$ represents a C1-C6 alkyl group; $R^4$ represents a hydrogen atom; $R^6$ represents $NR^7R^8$; and $R^7$ and $R^8$ are identical to or different from each other and each represents independently a C1-C6 alkyl group.

Embodiment 5

The compound according to Embodiment 1, wherein $R^2$ represents a hydrogen atom; $R^3$ represents a C1-C6 alkyl group; $R^4$ represents a hydrogen atom; and $R^6$ represents a phenyl group optionally having one or more substituents selected from Group D.

Embodiment 6

The compound according to Embodiment 1, wherein $R^2$ represents a hydrogen atom; $R^3$ represents a C1-C6 alkyl group; $R^4$ represents a hydrogen atom; $R^6$ represents $NR^7R^8$; and $R^7$ and $R^8$ are identical to or different from each other and each represents independently a C1-C6 alkyl group.

Embodiment 7

The compound according to Embodiment 1, wherein $R^1$ represents a methyl group.

Embodiment 8

The compound according to Embodiment 2, wherein $R^1$ represents a methyl group.

Embodiment 9

The compound according to Embodiment 3, wherein $R^1$ represents a methyl group.

Embodiment 10

The compound according to Embodiment 4, wherein $R^1$ represents a methyl group.

Embodiment 11

The compound according to Embodiment 5, wherein $R^1$ represents a methyl group.

Embodiment 12

The compound according to Embodiment 6, wherein $R^1$ represents a methyl group.

Embodiment 13

The compound according to any one of Embodiments 1 to 12, wherein $A^1$ represents a nitrogen atom.

Embodiment 14

The compound according to any one of Embodiments 1 to 12, wherein $A^1$ represents a nitrogen atom; and $R^5$ represents $CF_3$.

Embodiment 15

The compound according to any one of Embodiments 1 to 12, wherein $A^1$ represents a nitrogen atom; and m and n are each 2.

Embodiment 16

The compound according to any one of Embodiments 1 to 12, wherein $A^1$ represents a nitrogen atom; $R^5$ represents $CF_3$; and n is 2.

Next, the examples of the embodiments of the intermediate of the present invention include the following compounds.

Embodiment 21

An intermediate compound of the present invention, wherein $R^1$ represents a C1-C6 alkyl group.

Embodiment 22

The compound according to Embodiment 21, wherein $R^2$ represents a C1-C6 alkyl group, $C(O)OR^3$ or a hydrogen atom; $R^3$ represents a C1-C6 alkyl group; $R^4$ represents a C1-C6 alkyl group or a hydrogen atom; $R^6$ represents a C1-C6 alkyl group, a phenyl group optionally having one or more substituents selected from Group D, or $NR^7R^8$; and $R^7$ and $R^8$ are identical to or different from each other and each represents independently a C1-C6 alkyl group.

Embodiment 23

The compound according to Embodiment 21, wherein $R^2$ represents a C1-C6 alkyl group, $C(O)OR^3$ or a hydrogen atom; $R^3$ represents a C1-C6 alkyl group; $R^4$ represents a hydrogen atom; and $R^6$ represents a phenyl group optionally having one or more substituents selected from Group D.

Embodiment 24

The compound according to Embodiment 21, wherein $R^2$ represents a C1-C6 alkyl group, $C(O)OR^3$ or a represents a hydrogen atom; $R^6$ represents $NR^7R^8$; and $R^7$ and $R^8$ are identical to or different from each other and each represents independently a C1-C6 alkyl group.

Embodiment 25

The compound according to Embodiment 21, wherein $R^2$ represents a hydrogen atom; $R^3$ represents a C1-C6 alkyl group; $R^4$ represents a hydrogen atom; and $R^6$ represents a phenyl group optionally having one or more substituents selected from Group D.

Embodiment 26

The compound according to Embodiment 21, wherein $R^2$ represents a hydrogen atom; $R^3$ represents a C1-C6 alkyl group; $R^4$ represents a hydrogen atom; $R^6$ represents $NR^7R^8$; and $R^7$ and $R^8$ are identical to or different from each other and each represents independently a C1-C6 alkyl group.

Embodiment 27

The compound according to Embodiment 21, wherein $R^1$ represents a methyl group.

Embodiment 28

The compound according to Embodiment 22, wherein $R^1$ represents a methyl group.

Embodiment 29

The compound according to Embodiment 23, wherein $R^1$ represents a methyl group.

Embodiment 30

The compound according to Embodiment 24, wherein $R^1$ represents a methyl group.

Embodiment 31

The compound according to Embodiment 25, wherein $R^1$ represents a methyl group.

Embodiment 32

The compound according to Embodiment 26, wherein $R^1$ represents a methyl group.

Embodiment 33

The compound according to any one of Embodiments 21 to 32, wherein $A^1$ represents a nitrogen atom.

Embodiment 34

The compound according to any one of Embodiments 21 to 32, wherein $A^1$ represents a nitrogen atom; and $R^5$ represents $CF_3$.

Embodiment 35

The compound according to any one of Embodiments 21 to 32, wherein A' represents a nitrogen atom; and m and n are each 2.

Embodiment 36

The compound according to any one of Embodiments 21 to 32, wherein A' represents a nitrogen atom; $R^5$ represents $CF_3$; and n is 2.

Next, processes for preparing the compound of the present invention are explained below.

Process 1

A compound represented by formula (I) (hereinafter, referred to as Compound (I)) can be prepared by reacting a compound represented by formula (M1) (hereinafter referred to as Compound (M1)) with a compound represented by formula (M2) (hereinafter referred to as Compound (M2)) in the presence of a base.

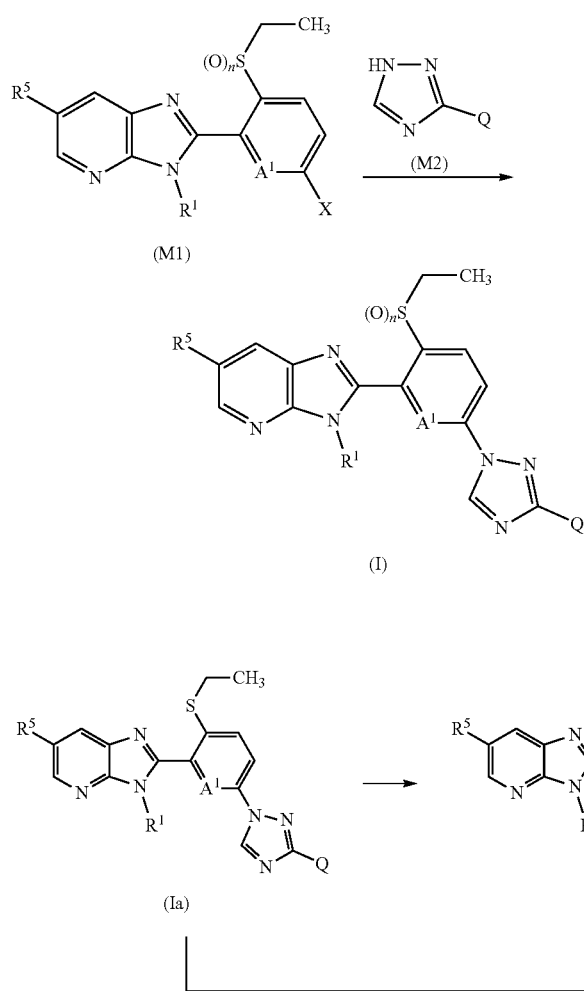

(M1)

(I)

metal hydrides (hereinafter, collectively referred to as alkali metal hydrides) such as sodium hydride.

In the reaction, the compound (M2) is used usually within a range of 0.5 to 2 molar ratio(s), and the base is used usually within a range of 1 to 5 molar ratio(s), as opposed to 1 mol of the compound (M1).

The reaction temperature is usually within a range of −20 to 120° C. The reaction period is usually within a range of 0.1 to 24 hours.

After completion of the reaction, water may be added to the reaction mixtures, the mixture is extracted with organic solvent(s), and the organic layer is worked up (for example, drying and concentration) to isolate the compound (I).

Each of the compound (M1) and the compound (M2) is a publicly known compound, or can be prepared according to a publicly known method.

Process 2

A compound represented by formula (Ib) (hereinafter referred to as Compound (Ib)) or a compound represented by formula (Ic) (hereinafter referred to as Compound (Ic)) can be prepared by oxidizing a compound represented by formula (Ia) (hereinafter referred to as Compound (Ia)).

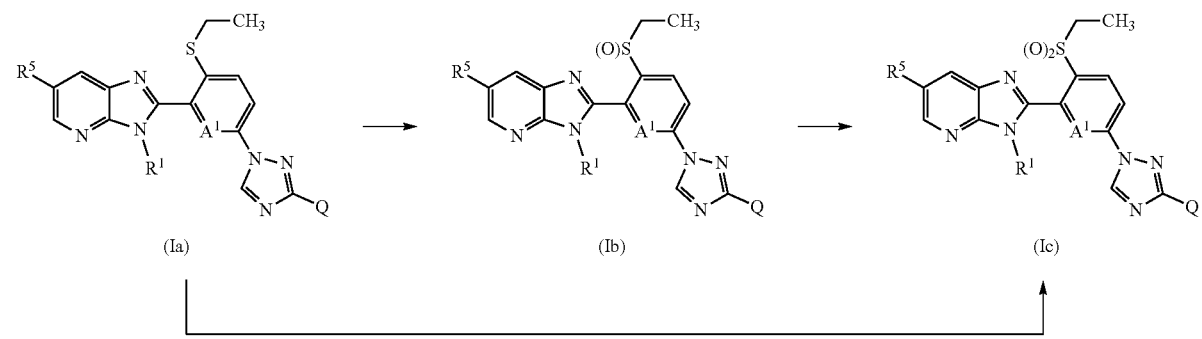

[wherein, the symbols have the same meanings as defined above]

The reaction is usually carried out in the presence of a solvent. Examples of the solvent used in the reaction include: ethers (hereinafter, collectively referred to as ethers) such as tetrahydrofuran (hereinafter referred to as THF), 1,4-dioxane, ethylene glycol dimethyl ether, methyl tert-butyl ether (hereinafter referred to as MTBE); hydrocarbons (hereinafter, collectively referred to as hydrocarbons) such as hexane, toluene and xylene; aprotic polar solvents (hereinafter, collectively referred to as aprotic polar solvents) such as N,N-dimethylformamide (hereinafter referred to as DMF), N-methylpyrrolidone (hereinafter referred to as NMP), and dimethylsulfoxide (hereinafter referred to as DMSO); halogenated hydrocarbons (hereinafter, collectively referred to as halogenated hydrocarbons) such as chloroform; nitriles (hereinafter, collectively referred to as nitriles) such as acetonitrile; and mixtures thereof.

Examples of the base used in the reaction include: organic bases (hereinafter, collectively referred to as organic bases) such as triethylamine, diisopropylethylamine, pyridine, and 4-(dimethylamino)pyridine; alkali metal carbonates (hereinafter, collectively referred to as alkali metal carbonates) such as sodium carbonate and potassium carbonate; and alkali

[wherein, the symbols have the same meanings as defined above].

First, a method for preparing the compound (Ib) from the compound (Ia) is described.

The reaction is usually carried out in a solvent. Examples of the solvent used in the reaction include halogenated hydrocarbons; nitriles; alcohols (hereinafter, collectively referred to as alcohols) such as methanol and ethanol; acetic acid; water; and mixtures thereof.

Examples of the oxidizing agent used in the reaction include sodium periodate, m-chloroperoxybenzoic acid (hereinafter referred to as mCPBA) and hydrogen peroxide.

When hydrogen peroxide is used as the oxidizing agent, sodium carbonate or a catalyst may be added as needed.

Examples of the catalyst used in the reaction include tungstic acid, and sodium tungstate.

In the reaction, the oxidizing agent is used usually within a range of 1 to 1.2 molar ratio(s), sodium carbonate is used usually within a range of 0.01 to 1 molar ratio(s), and the catalyst is used usually within a range of 0.01 to 0.5 molar ratio(s), as opposed to 1 mol of the compound (Ia).

The reaction temperature is usually within a range of −20° C. to 80° C. The reaction period is usually within a range of 0.1 to 12 hours.

After completion of the reaction, water may be added to the reaction mixtures, the mixture is extracted with an organic solvent(s), and if necessary, the organic layer is washed with an aqueous solution of a reducing agent (for example, sodium sulfite, and sodium thiosulfate) and an aqueous solution of a base (for example, sodium hydrogen carbonate). The organic layer may be dried and concentrated to obtain the compound (Ib).

Next, a method for preparing the compound (Ic) from the compound (Ib) is described.

The reaction is usually carried out in a solvent. Examples of the solvent used in the reaction include halogenated hydrocarbons; nitriles; alcohols; acetic acid; water; and mixtures thereof.

Examples of the oxidizing agent used in the reaction include mCPBA and hydrogen peroxide.

When hydrogen peroxide is used as the oxidizing agent, a base or a catalyst may be added as needed.

Examples of the base used in the reaction include sodium carbonate.

Examples of the catalyst used in the reaction include sodium tungstate.

In the reaction, the oxidizing agent is used usually within a range of 1 to 2 molar ratio(s), the base is used usually within a range of 0.01 to 1 molar ratio(s), and the catalyst is used usually within a range of 0.01 to 0.5 molar ratio(s), as opposed to 1 mol of the compound (Ib).

The reaction temperature is usually within a range of −20° C. to 120° C. The reaction period is usually within a range of 0.1 to 12 hours.

After completion of the reaction, water may be added to the reaction mixtures, the mixture is extracted with an organic solvent(s), and if necessary, the organic layer is washed with an aqueous solution of a reducing agent (for example, sodium sulfite, and sodium thiosulfate) and an aqueous solution of a base (for example, sodium hydrogen carbonate). The organic layer may be dried and concentrated to obtain the compound (Ic).

Also, the compound (Ic) can be prepared by reacting the compound (Ia) with the oxidizing agent in one step reaction (one-pot).

The reaction may be carried out by using the oxidizing agent in a ratio usually of 2 to 5 molar ratios as opposed to 1 mol of the compound (Ia) according to the method for preparing the compound (Ic) from the compound (Ib).

Process 3

A compound represented by formula (Id) (hereinafter referred to as Compound (Id)) can be prepared by reacting a compound represented by formula (M5) (hereinafter referred to as Compound (M5)) with a compound represented by formula (M6) (hereinafter referred to as Compound (M6)).

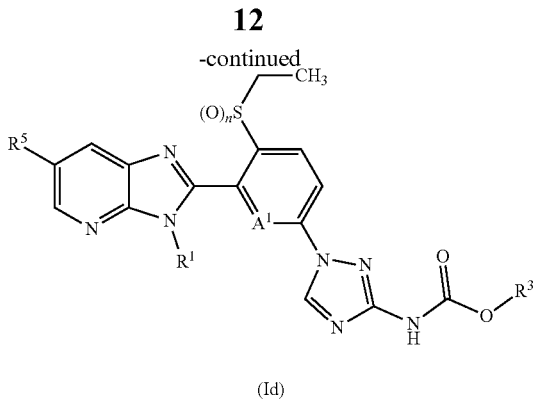

(Id)

[wherein, $X^2$ represents a chlorine atom or $OCO(O)R^3$; and the symbols have the same meanings as defined above]

The reaction is usually carried out in the presence of a solvent. Examples of the solvent used in the reaction include ethers; hydrocarbons; halogenated hydrocarbons; nitriles; aprotic polar solvents; and mixtures thereof.

In the reaction, a base may be used as needed. Examples of the base used in the reaction include organic bases and alkali metal carbonates.

In the reaction, the compound (M4) is used usually within a range of 1 to 1.5 molar ratio(s) and the base is used usually within a range of 1 to 5 molar ratio(s), as opposed to 1 mol of the compound (M5).

The reaction temperature is usually within a range of 0° C. to 120° C. The reaction period is usually within a range of 0.1 to 24 hours.

After completion of the reaction, water may be added to the reaction mixtures, the mixture is extracted with an organic solvent(s), and the organic layer is worked up (for example, drying and concentration) to isolate the compound (Id).

The compound (M5) can be prepared according to the method described in WO2015/133603 A1. The compound (M6) is a publicly known compound, or can be prepared according to a publicly known method.

Process 4

A compound represented by formula (Ie) (hereinafter referred to as Compound (Ie)) can be prepared by reacting a compound represented by formula (M7) (hereinafter referred to as Compound (M7)) with the compound (M6).

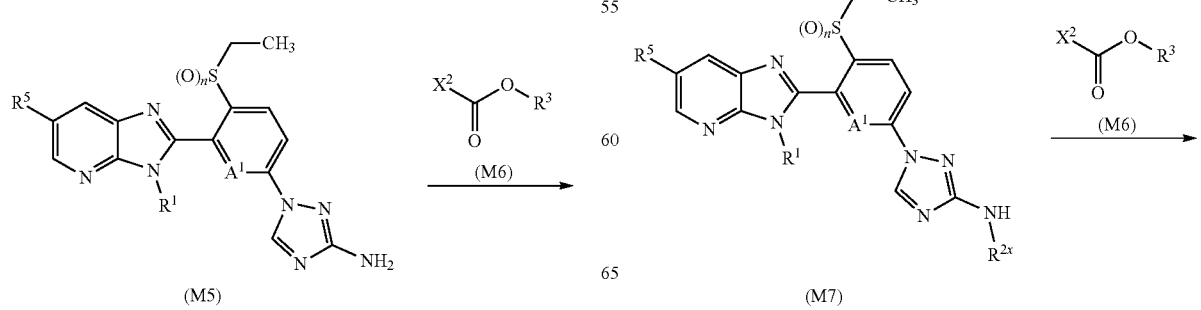

-continued

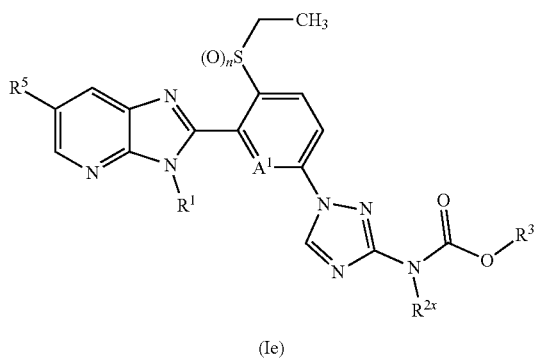

(Ie)

[wherein, $R^{2x}$ represents a C1-C6 alkyl group optionally having one or more halogen atoms, or a C3-C6 cycloalkyl group optionally having one or more halogen atoms; and the other symbols have the same meanings as defined above]

The reaction can be carried out according to the method described in the Process 3.

The compound (M7) can be prepared according to the method described in WO2015/133603 A1.

Process 5

A compound represented by formula (If) (hereinafter referred to as Compound (If)) can be prepared by reacting the compound (Id) with the compound (M6) in the presence of a base.

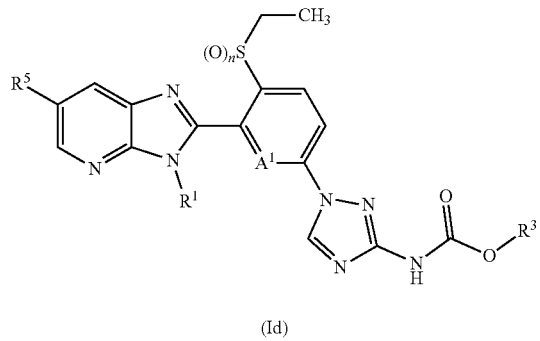

(Id)

[wherein, the symbols have the same meanings as defined above]

The reaction is usually carried out in the presence of a solvent. Examples of the solvent used in the reaction include ethers; hydrocarbons; halogenated hydrocarbons; nitriles; aprotic polar solvents; and mixtures thereof.

Examples of the base used in the reaction include organic bases and alkali metal carbonates.

In the reaction, the compound (M6) is used usually within a range of 1 to 5 molar ratio(s) and the base is used usually within a range of 1 to 5 molar ratio(s), as opposed to 1 mol of the compound (Id).

The reaction temperature is usually within a range of 0° C. to 120° C. The reaction period is usually within a range of 0.1 to 24 hours.

After completion of the reaction, water may be added to the reaction mixtures, the mixture is extracted with an organic solvent(s), and the organic layer is worked up (for example, drying and concentration) to isolate the compound (If).

Process 6

The compound represented by formula (If) can be prepared by reacting the compound (M5) with the compound (M6) in the presence of a base.

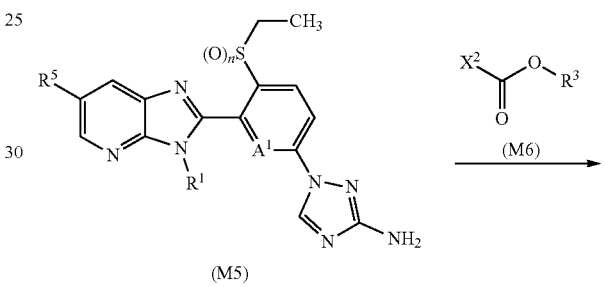

(M5)

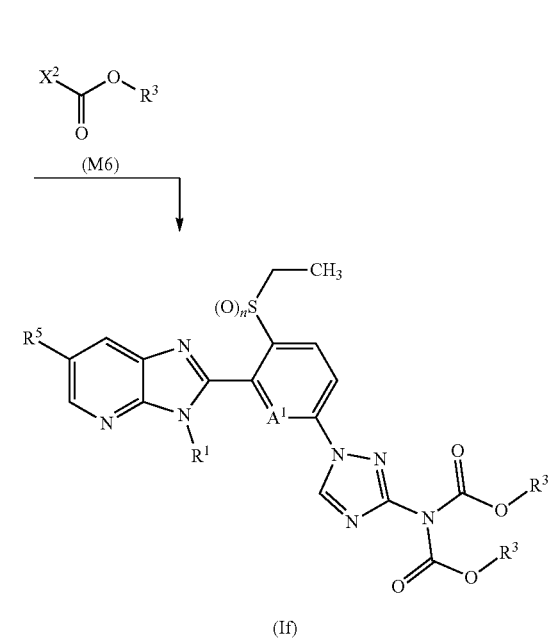

(If)

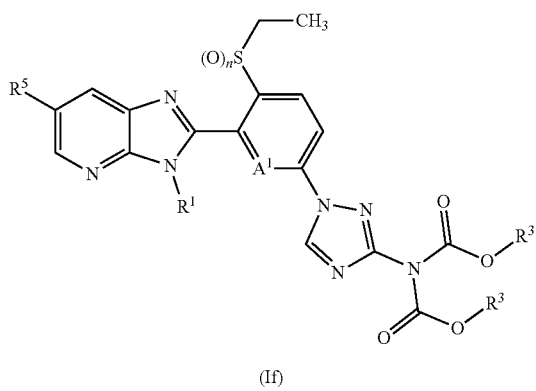

(If)

[wherein, the symbols have the same meanings as defined above]

The reaction is usually carried out in the presence of a solvent. Examples of the solvent used in the reaction include ethers; hydrocarbons; halogenated hydrocarbons; nitriles; aprotic polar solvents; and mixtures thereof.

Examples of the base used in the reaction include organic bases and alkali metal carbonates.

In the reaction, the compound (M6) is used usually within a range of 1.5 to 5 molar ratio(s) and the base is used usually within a range of 2 to 5 molar ratio(s), as opposed to 1 mol of the compound (M5).

The reaction temperature is usually within a range of 0° C. to 120° C. The reaction period is usually within a range of 0.1 to 24 hours.

After completion of the reaction, water may be added to the reaction mixtures, the mixture is extracted with an organic solvent(s), and the organic layer is worked up (for example, drying and concentration) to isolate the compound (If).

Process 7

A compound represented by formula (Ij) (hereinafter referred to as Compound (Ij)) can be prepared by reacting the compound (M5) with a compound represented by formula (M10) (hereinafter referred to as Compound (M10)).

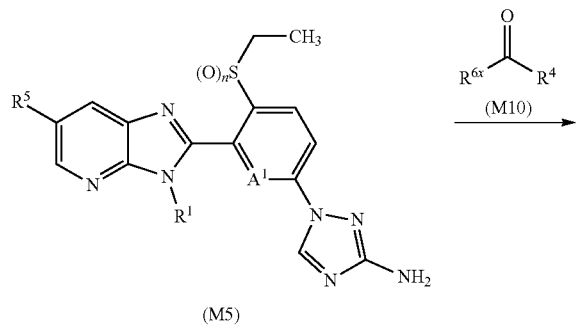

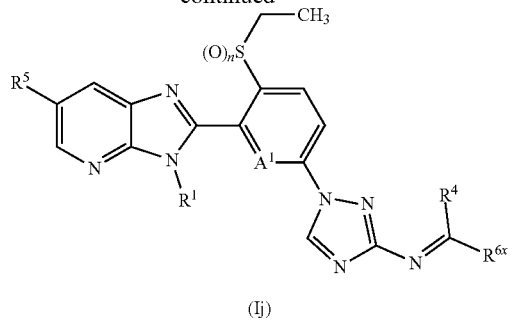

(Ij)

[wherein, $R^{6x}$ represents a C1-C6 alkyl group optionally having one or more halogen atoms, or a phenyl group optionally having one or more substituents selected from Group D; and the other symbols have the same meanings as defined above]

The reaction is usually carried out in the presence of a solvent. Examples of the solvent used in the reaction include ethers; hydrocarbons; halogenated hydrocarbons; nitriles; aprotic polar solvents; and mixtures thereof. The compound (M10) may be also used as the solvent.

The reaction may be carried out by adding an acid as needed.

Examples of the acid used in the reaction include mineral acids such as hydrogen chloride and sulfuric acid; sulfonic acids such as para-toluenesulfonic acid.

In the reaction, the compound (M10) is used usually within a range of 1 to 5 molar ratio(s) and the acid is used usually within a range of 0.1 to 2 molar ratio(s), as opposed to 1 mol of the compound (M5).

The reaction temperature is usually within a range of 0° C. to 150° C. The reaction period is usually within a range of 0.1 to 24 hours.

After completion of the reaction, water may be added to the reaction mixtures, the mixture is extracted with an organic solvent(s), and the organic layer is worked up (for example, drying and concentration) to isolate the compound (Ij).

The compound (M10) is a publicly known compound, or can be prepared according to a publicly known method.

Process 8

A compound represented by formula (II) (hereinafter, the compound may be referred to as Compound (II)) can be prepared by reacting a compound represented by formula (M13) (hereinafter referred to as Compound (M13)) with the compound (M2) in the presence of a base.

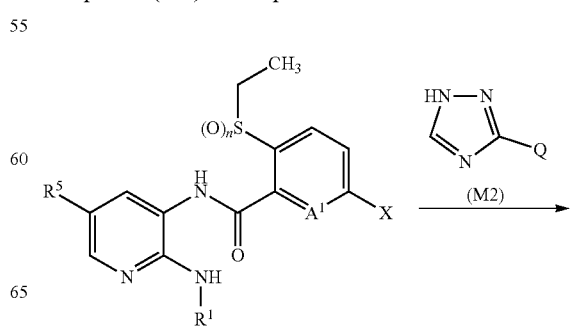

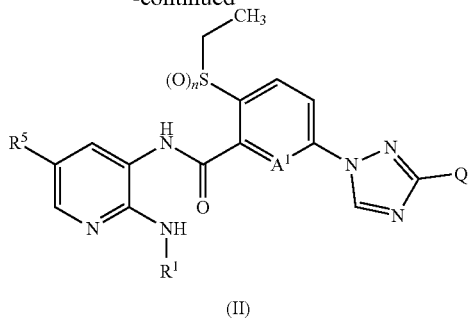

(II)

[wherein, the symbols have the same meanings as defined above]

The reaction can be carried out according to the method described in the Process 1.

The compound (M13) can be prepared according to the method described in WO2012/086848 A1 or WO2013/018928 A1.

Process 9

The compound represented by formula (I) can be prepared by reacting the compound (II) in the presence of an acid.

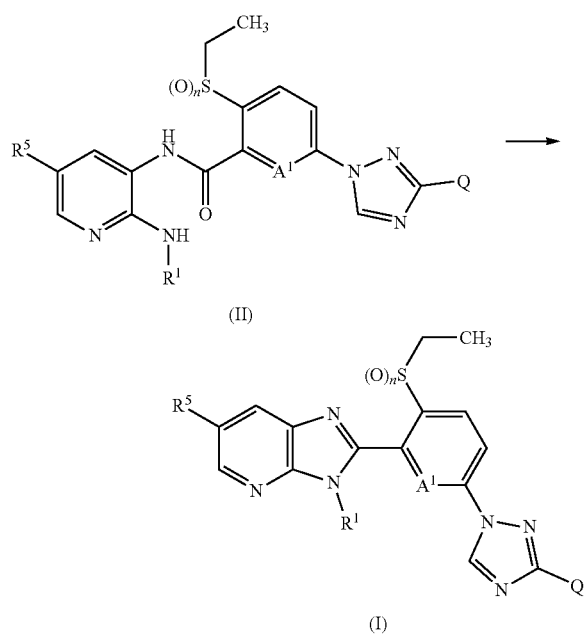

[wherein, the symbols have the same meanings as defined above]

The reaction is usually carried out in the presence of a solvent. Examples of the solvent used in the reaction include ethers; halogenated hydrocarbons; hydrocarbons; aprotic polar solvents; and mixtures thereof.

Examples of the acid used in the reaction include sulfonic acids such as para-toluenesulfonic acid; carboxylic acids such as acetic acid and lactic acid; and polyphosphoric acid.

In the reaction, the acid is used usually within a range of 0.1 to 5 molar ratio(s), as opposed to 1 mol of the compound (II).

The reaction temperature is usually within a range of 0° C. to 200° C. The reaction period is usually within a range of 0.1 to 24 hours.

After completion of the reaction, water may be added to the reaction mixtures, the mixture is extracted with an organic solvent(s), and the organic layer is worked up (for example, drying and concentration) to isolate the compound Process 10

The compound (II) can be prepared according to the scheme described below.

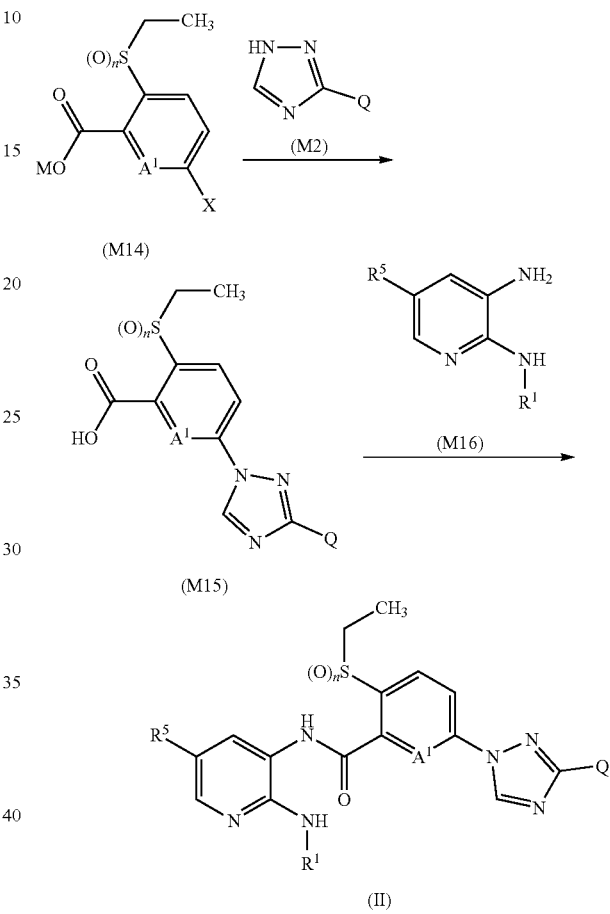

[wherein, M represents a hydrogen atom, a sodium atom, or a potassium atom; and the other symbols have the same meanings as defined above]

First, a first step of preparing a compound represented by formula (M15) (hereinafter referred to as Compound (M15)) from a compound represented by formula (M14) (hereinafter referred to as Compound (M14)) is described.

The reaction can be carried out according to the method described in the Process 1.

Next, a second step of preparing the compound (II) from the compound (M15) is described.

The compound (II) can be prepared by reacting the compound (M15) with a compound represented by formula (M16) (hereinafter referred to as Compound (M16)) in the presence of a condensing agent.

The reaction is usually carried out in the presence of a solvent. Examples of the solvent used in the reaction include ethers; nitriles; aprotic polar solvents; and mixtures thereof.

Examples of the condensing agent used in the reaction include carbodiimides such as 1-ethyl-3-(3-dimethylaminopropyl)carbodiimide hydrochloride (hereinafter referred to as EDCI hydrochloride) and 1,3-dicyclohexylcarbodiimide.

In the reaction, a catalyst may be added as needed. Examples of the catalyst used in the reaction include 1-hydroxybenzotriazole (hereinafter referred to as HOBt).

In the reaction, the compound (M16) is used usually within a range of 1 to 5 molar ratio(s), the condensing agent is used usually within a range of 1 to 5 molar ratio(s), and the catalyst is used usually within a range of 0.01 to 1 molar ratio(s), as opposed to 1 mol of the compound (M15).

The reaction temperature is usually within a range of 0° C. to 120° C. The reaction period is usually within a range of 0.1 to 24 hours.

After completion of the reaction, water may be added to the reaction mixtures, the mixture is extracted with an organic solvent(s), and the organic layer is worked up (for example, drying and concentration) to isolate the compound (II).

The compound (M14) and the compound (M16) is a publicly known compound, or can be prepared according to a publicly known method.

Next, specific examples of the compound of the present invention are shown below.

Herein, Me represents a methyl group, Et represents an ethyl group, Pr represents a propyl group, i-Pr represents an isopropyl group, Bu represents a butyl group, i-Bu represents an isobutyl group, s-Bu represents a sec-butyl group, t-Bu represents a tert-butyl group, c-Pr represents a cyclopropyl group, Ph represents a phenyl group, Bn represents benzyl group, and Boc represents tert-butoxycarbonyl group. When Ph and Bn have a substituent, the substituent is described together with a substitution position before the symbol. For example, 4-CF$_3$-Ph represents a 4-(trifluoromethyl)phenyl group, 2,4-(NO$_2$)$_2$-Ph represents a 2,4-dinitrophenyl group, 2,4,6-Me$_3$-Ph represents 2,4,6-trimethylphenyl group, and 4-OMe-Bn represents 4-methoxybenzyl group.

A compound represented by formula (L-1):

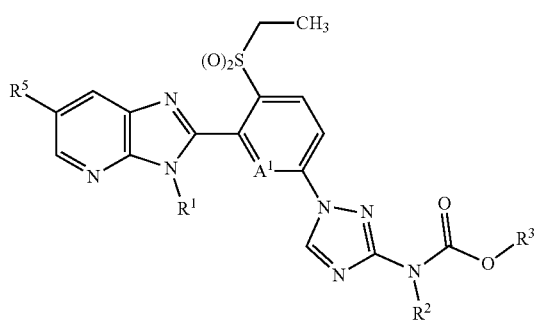

(L-1)

(hereinafter referred to as Compound (L-1))
wherein A$^1$ represents CH; R$^5$ represents CF$_3$; R$^1$ represents a methyl group; and R$^2$ and R$^3$ represent any one of the substituents described in Table 1 or 2 (hereinafter referred to as Compound Class SX1).

TABLE 1

| R$^2$ | R$^3$ |
|---|---|
| H | Me |
| H | Et |
| H | Pr |
| H | i-Pr |

TABLE 1-continued

| R$^2$ | R$^3$ |
|---|---|
| H | Bu |
| H | i-Bu |
| H | s-Bu |
| H | t-Bu |
| H | Ph |
| H | Bn |
| H | 4-OMe-Bn |
| H | 4-NO$_2$-Bn |
| Me | Me |
| Me | Et |
| Me | Pr |
| Me | i-Pr |
| Me | Bu |
| Me | i-Bu |
| Me | s-Bu |
| Me | t-Bu |
| Me | Ph |
| Me | Bn |
| Me | 4-OMe-Bn |
| Me | 4-NO$_2$-Bn |

TABLE 2

| R$^2$ | R$^3$ |
|---|---|
| c-Pr | Me |
| c-Pr | Et |
| c-Pr | Pr |
| c-Pr | i-Pr |
| c-Pr | Bu |
| c-Pr | i-Bu |
| c-Pr | s-Bu |
| c-Pr | t-Bu |
| c-Pr | Ph |
| c-Pr | Bn |
| c-Pr | 4-OMe-Bn |
| c-Pr | 4-NO$_2$-Bn |
| C(O)OMe | Me |
| C(O)OEt | Et |
| C(O)OPr | Pr |
| C(O)Oi-Pr | i-Pr |
| C(O)OBu | Bu |
| C(O)Oi-Bu | i-Bu |
| C(O)Os-Bu | s-Bu |
| C(O)Ot-Bu | t-Bu |
| C(O)OPh | Ph |
| C(O)OBn | Bn |
| C(O)O(4-OMe-Bn) | 4-OMe-Bn |
| C(O)O(4-NO$_2$-Bn) | 4-NO$_2$-Bn |

A compound (L-1), wherein A$^1$ represents CH; R$^5$ represents a pentafluoroethyl group; R$^1$ represents a methyl group; and R$^2$ and R$^3$ represent any one of the substituents described in Table 1 or 2 (hereinafter referred to as Compound Class SX2).

A compound (L-1), wherein A$^1$ represents CH; R$^5$ represents trifluoromethylsulfonyl group; R$^1$ represents a methyl group; and R$^2$ and R$^3$ represent any one of the substituents described in Table 1 or 2 (hereinafter referred to as Compound Class SX3).

A compound (L-1), wherein A$^1$ represents a nitrogen atom; R$^5$ represents a trifluoromethyl group; R$^1$ represents a methyl group; and R$^2$ and R$^3$ represent any one of the substituents described in Table 1 or 2 (hereinafter referred to as Compound Class SX4).

A compound (L-1), wherein A$^1$ represents a nitrogen atom; R$^5$ represents a pentafluoroethyl group; R$^1$ represents a methyl group; and R$^2$ and R$^3$ represent any one of the substituents described in Table 1 or 2 (hereinafter referred to as Compound Class SX5).

A compound (L-1), wherein A$^1$ represents a nitrogen atom; R$^5$ represents trifluoromethylsulfonyl group; R$^1$ represents a methyl group; and $R^2$ and $R^3$ represent any one of the substituents described in Table 1 or 2 (hereinafter referred to as Compound Class SX6).

A compound represented by formula (L-2):

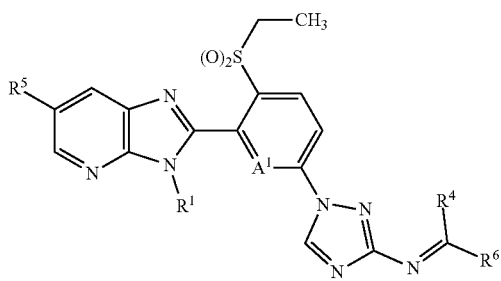

(L-2)

(hereinafter referred to as Compound (L-2))

wherein $A^1$ represents CH; $R^5$ represents trifluoromethyl group; $R^1$ represents a methyl group; and $R^4$ and $R^6$ represent any one of the substituents described in Table 3 or 4 (hereinafter referred to as Compound Class SX7).

TABLE 3

| $R^4$ | $R^6$ |
|---|---|
| Me | Me |
| Et | Et |
| Pr | Pr |
| Ph | Ph |
| H | Et |
| H | Pr |
| H | Ph |
| H | 4-OMe-Ph |
| H | 4-NO$_2$-Ph |
| H | 4-CF$_3$-Ph |
| H | 4-CN-Ph |
| H | 4-Cl-Ph |
| H | NMe$_2$ |
| H | NMeEt |
| H | NMePr |

TABLE 4

| $R^4$ | $R^6$ |
|---|---|
| Me | Et |
| Me | Pr |
| Me | Ph |
| Me | 4-OMe-Ph |
| Me | 4-NO$_2$-Ph |
| Me | 4-CF$_3$-Ph |
| Me | 4-CN-Ph |
| Me | 4-Cl-Ph |
| Me | NMe$_2$ |
| Me | NMeEt |
| Me | NMePr |
| —CH$_2$CH$_2$CH$_2$CH$_2$— | |
| —CH$_2$CH$_2$CH$_2$CH$_2$CH$_2$— | |

A compound (L-2), wherein $A^1$ represents CH; $R^5$ represents a pentafluoroethyl group; $R^1$ represents a methyl group; and $R^4$ and $R^6$ represent any one of the substituents described in Table 3 or 4 (hereinafter referred to as Compound Class SX8).

A compound (L-2), wherein $A^1$ represents CH; $R^5$ represents trifluoromethylsulfonyl group; $R^1$ represents a methyl group; and $R^4$ and $R^6$ represent any one of the substituents described in Table 3 or 4 (hereinafter referred to as Compound Class SX9).

A compound (L-2), wherein $A^1$ represents a nitrogen atom; $R^5$ represents a trifluoromethyl group; $R^1$ represents a methyl group; and $R^4$ and $R^6$ represent any one of the substituents described in Table 3 or 4 (hereinafter referred to as Compound Class SX10).

A compound (L-2), wherein $A^1$ represents a nitrogen atom; $R^5$ represents a pentafluoroethyl group; $R^1$ represents a methyl group; and $R^4$ and $R^6$ represent any one of the substituents described in Table 3 or 4 (hereinafter referred to as Compound Class SX11).

A compound (L-2), wherein $A^1$ represents a nitrogen atom; $R^5$ represents trifluoromethylsulfonyl group; $R^1$ represents a methyl group; and $R^4$ and $R^6$ represent any one of the substituents described in Table 3 or 4 (hereinafter referred to as Compound Class SX12).

Next, specific examples of the intermediate of the present invention are shown below.

A compound represented by formula (P-1):

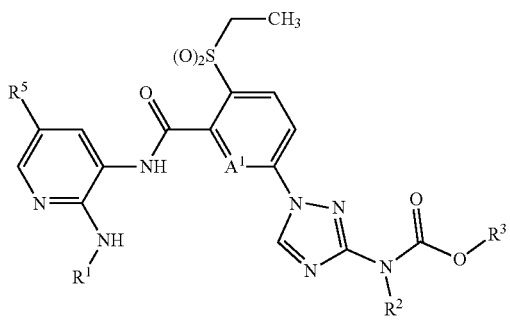

(P-1)

(hereinafter referred to as Compound (P-1))

wherein $A^1$ represents CH; $R^5$ represents a trifluoromethyl group; $R^1$ represents a methyl group; and $R^2$ and $R^3$ represent any one of the substituents described in Table 1 or 2 (hereinafter referred to as Compound Class SX13).

A compound (P-1), wherein $A^1$ represents CH; $R^5$ represents a pentafluoroethyl group; $R^1$ represents a methyl group; and $R^2$ and $R^3$ represent any one of the substituents described in Table 1 or 2 (hereinafter referred to as Compound Class SX14).

A compound (P-1), wherein $A^1$ represents CH; $R^5$ represents trifluoromethylsulfonyl group; $R^1$ represents a methyl group; and $R^2$ and $R^3$ represent any one of the substituents described in Table 1 or 2 (hereinafter referred to as Compound Class SX15).

A compound (P-1), wherein $A^1$ represents a nitrogen atom; $R^5$ represents a trifluoromethyl group; $R^1$ represents a methyl group; and $R^2$ and $R^3$ represent any one of the substituents described in Table 1 or 2 (hereinafter referred to as Compound Class SX16).

A compound (P-1), wherein $A^1$ represents a nitrogen atom; $R^5$ represents a pentafluoroethyl group; $R^1$ represents a methyl group; and $R^2$ and $R^3$ represent any one of the substituents described in Table 1 or 2 (hereinafter referred to as Compound Class SX17).

A compound (P-1), wherein $A^1$ represents a nitrogen atom; $R^5$ represents trifluoromethylsulfonyl group; $R^1$ represents a methyl group; and $R^2$ and $R^3$ represent any one of the substituents described in Table 1 or 2 (hereinafter referred to as Compound Class SX18).

A compound represented by formula (P-2):

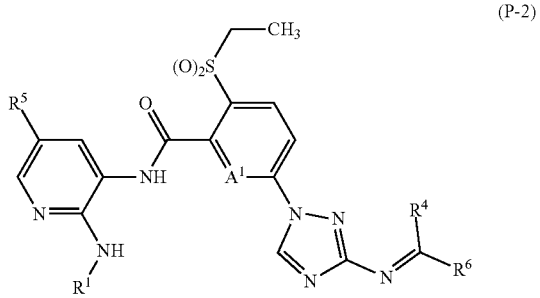

(P-2)

(hereinafter referred to as Compound (P-2))
wherein $A^1$ represents CH; $R^5$ represents trifluoromethyl group; $R^4$ represents a methyl group; and $R^4$ and $R^6$ represent any one of the substituents described in Table 3 or 4 (hereinafter referred to as Compound Class SX19).

A compound (P-2), wherein $A^1$ represents CH; $R^5$ represents a pentafluoroethyl group; $R^1$ represents a methyl group; and $R^4$ and $R^6$ represent any one of the substituents described in Table 3 or 4 (hereinafter referred to as Compound Class SX20).

A compound (P-2), wherein $A^1$ represents CH; $R^5$ represents trifluoromethylsulfonyl group; $R^1$ represents a methyl group; and $R^4$ and $R^6$ represent any one of the substituents described in Table 3 or 4 (hereinafter referred to as Compound Class SX21).

A compound (P-2), wherein $A^1$ represents a nitrogen atom; $R^5$ represents a trifluoromethyl group; $R^4$ represents a methyl group; and $R^4$ and $R^6$ represent any one of the substituents described in Table 3 or 4 (hereinafter referred to as Compound Class SX22).

A compound (P-2), wherein $A^1$ represents a nitrogen atom; $R^5$ represents a pentafluoroethyl group; $R^1$ represents a methyl group; and $R^4$ and $R^6$ represent any one of the substituents described in Table 3 or 4 (hereinafter referred to as Compound Class SX23).

A compound (P-2), wherein $A^1$ represents a nitrogen atom; $R^5$ represents trifluoromethylsulfonyl group; $R^1$ represents a methyl group; and $R^4$ and $R^6$ represent any one of the substituents described in Table 3 or 4 (hereinafter referred to as Compound Class SX24).

The compound of the present invention may be mixed or combined with one or more ingredient(s) (hereinafter referred to as Present ingredient) selected from the group consisting of Group (a), Group (b), Group (c), Group (d), and Group (e).

The above-mentioned mixing or combining means a use of the compound of the present invention and the present ingredient at the same time, separately, or at certain intervals.

When the compound of the present invention and the present ingredient are used at the same time, the compound of the present invention and the present ingredient may each be contained in separate formulations respectively, or may be contained in the same one formulation.

One aspect of the present invention relates to a composition that comprises one or more ingredient(s) selected from the group consisting of Group (a) and Group (b), as well as the compound of the present invention.

Group (a) is a group consisting of Acetylcholinesterase inhibitors (e.g., carbamate insecticides and organophosphorus insecticides), GABA-gated chloride channel antagonists (e.g., phenylpyrazol insecticides), Sodium channel modulators (e.g., pyrethroid insecticides), Nicotinic acetylcholine receptor competitive modulators (e.g., neonicotinoid insecticides), Nicotinic acetylcholine receptor allosteric modulators, Glutamatergic chloride ion channel allosteric modulators (e.g., macrolide insecticides), Juvenile hormone mimics, Multisite inhibitors, Chordotonal organ TRPV channel modulators, Mites growth inhibitors, Mitochondrial ATP biosynthetic enzyme inhibitors, Uncoupler of oxidative phosphorylation, Nicotinic acetylcholine receptor channel blockers (e.g., Nereistoxin insecticides), Chitin synthesis inhibitors, Molting inhibitors, Ecdysone receptor agonists, Octopamine receptor agonists, Inhibitors for mitochondrial electron transport system complex I, II, III and IV, Voltage-dependent sodium channel blockers, Acetyl-CoA carboxylase inhibitors, Ryanodine receptor modulators (e.g., Diamide-based insecticides), Chordotonal organ modulators, Microbial pesticides, and the other insecticidal, miticidal or nematicidal active ingredients. These ingredients are classified as a class based on the mechanism of action of IRAC.

Group (b) is a group consisting of Nucleic acid synthesis inhibitors (e.g., phenylamide fungicides and Acylamino acid fungicides), Cell division and cytoskeletal inhibitors (e.g., MBC fungicides), Respiratory inhibitors (e.g., QoI fungicides and QiI fungicides), Amino acid synthesis and protein synthesis inhibitors (e.g., anilinopyridine fungicides), Signal transduction inhibitors, Lipid synthesis and membrane synthesis inhibitors, Sterol biosynthesis inhibitors (e.g., DMI fungicides such as triazole), Cell wall synthesis inhibitors, Melanin synthesis inhibitors, Plant defense inducers, Other action point contact active fungicides, Microbial fungicides, and the other fungicidal active ingredients. These are classified as a class based on the mechanism of action of FRAC.

Group (c) is a plant growth modulating ingredients group which consists of Plant growth modulating ingredients, Mycorrhizal fungi, and Root nodule bacteria.

Group (d) is a phytotoxicity reducing ingredient group, which reduce the phytotoxicity against the crop when used in admixture with the other chemicals.

Group (e) is a synergist group, which enhance the efficacy when used in admixture with the other chemicals.

Examples of the combination of the present ingredient and the compound of the present invention are described below. For example, alanycarb+SX represents a combination of alanycarb and SX.

The symbol of "SX" represents any one of the compound of the present invention selected from the compound Class SX1 to SX12. In addition, all of the present ingredients as described below are publicly known ingredients, and are available from commercial formulation or may be prepared by a publicly known method. If the present ingredient is a bacterium, it is available also from the bacterial authority depository. The numerical number in bracket represents a CAS RN (registered trademark).

Combination of the present ingredient of the above group (a) and the compound of the present invention:
abamectin+SX, acephate+SX, acequinocyl+SX, acetamiprid+SX, acrinathrin+SX, acynonapyr+SX, afidopyropen+SX, afoxolaner+SX, alanycarb+SX, aldicarb+SX, allethrin+SX, alpha-cypermethrin+SX, alpha-endosulfan+SX, aluminium phosphide+SX, amitraz+SX, azadirachtin+SX, azamethiphos+SX, azinphos-ethyl+SX, azinphos-methyl+SX, azocyclotin+SX, bendiocarb+SX, benfluthrin+SX, benfuracarb+SX, bensultap+SX, benzoximate+SX, benzpyrimoxan+SX, beta-cyfluthrin+SX, beta-cypermethrin+SX, bifenazate+SX, bifenthrin+SX, bioallethrin+SX, bioresmethrin+SX, bistrifluron+SX, borax+SX, boric acid+SX, broflanilide+SX, bromopropylate+SX, buprofezin+SX, butocarboxim+SX, butoxycarboxim+SX, cadusafos+SX, calcium cyanide+SX, calcium phosphide+SX, carbaryl+SX, carbofuran+SX, carbosulfan+SX, cartap hydrochloride+SX, cartap+SX, chinomethionat+SX, chlorantraniliprole+SX, chlordane+SX, chlorethoxyfos+SX, chlorfenapyr+SX, chlorfenvinphos+SX, chlorfluazuron+SX, chlormephos+SX, chloropicrin+SX, chlorpyrifos+SX, chlorpyrifos-methyl+SX, chromafenozide+SX, clofentezine+SX, clothianidin+SX, coumaphos+SX, cryolite+SX, cyanophos+SX, cyantraniliprole+SX, cycloniliprole+SX, cycloprothrin+SX, cycloxaprid+SX, cyenopyrafen+SX, cyflumetofen+SX, cyfluthrin+SX, cyhalodiamide+SX, cyhalothrin+SX, cyhexatin+SX, cypermethrin+SX, cyphenothrin+SX, cyromazine+SX, dazomet+SX, deltamethrin+SX, demeton-S-methyl+SX, diafenthiuron+SX, diazinon+SX, dichlorvos+SX, dicloromezotiaz+SX, dicofol+SX, dicrotophos+SX, diflovidazin+SX, diflubenzuron+SX, difluthrin+SX, dimethoate+SX, dimethylvinphos+SX, dinotefuran+SX, disodium octaborate+SX, disulfoton+SX, DNOC (2-methyl-4,6-dinitrophenol)+SX, doramectin+SX, emamectin-benzoate+SX, empenthrin+SX, endosulfan+SX, EPN (O-ethyl O-(4-nitrophenyl) phenylphosphonothioate)+SX, epsilon-metofluthrin+SX, epsilon-momfluorothrin+SX, esfenvalerate+SX, ethiofencarb+SX, ethion+SX, ethiprole+SX, ethoprophos+SX, etofenprox+SX, etoxazole+SX, famphur+SX, fenamiphos+SX, fenazaquin+SX, fenbutatin oxide+SX, fenitrothion+SX, fenobucarb+SX, fenoxycarb+SX, fenpropathrin+SX, fenpyroximate+SX, fenthion+SX, fenvalerate+SX, fipronil+SX, flometoquin+SX, flonicamid+SX, fluacrypyrim+SX, fluazaindolizine+SX, fluazuron+SX, flubendiamide+SX, flucycloxuron+SX, flucythrinate+SX, fluensulfone+SX, flufenoprox+SX, flufenoxuron+SX, flufiprole+SX, flumethrin+SX, fluopyram+SX, flupyradifurone+SX, flupyrimin+SX, fluralaner+SX, fluvalinate+SX, fluxametamide+SX, formetanate+SX, fosthiazate+SX, furamethrin+SX, furathiocarb+SX, gamma-cyhalothrin+SX, halfenprox+SX, halofenozide+SX, heptafluthrin+SX, heptenophos+SX, hexaflumuron+SX, hexythiazox+SX, hydramethylnon+SX, hydroprene+SX, imicyafos+SX, imidacloprid+SX, imiprothrin+SX, indoxacarb+SX, isofenphos+SX, isoprocarb+SX, isopropyl-O-(methoxyaminothiophosphoryl)salicylate+SX, isoxathion+SX, ivermectin+SX, kadethrin+SX, kappa-tefluthrin+SX, kappa-bifenthrin+SX, kinoprene+SX, lambda-cyhalothrin+SX, lepimectin+SX, lime sulfur+SX, lufenuron+SX, machine oil+SX, malathion+SX, mecarbam+SX, meperfluthrin+SX, metaflumizone+SX, metam+SX, methamidophos+SX, methidathion+SX, methiocarb+SX, methomyl+SX, methoprene+SX, methoxychlor+SX, methoxyfenozide+SX, methyl bromide+SX, metofluthrin+SX, metolcarb+SX, metoxadiazone+SX, mevinphos+SX, milbemectin+SX, milbemycin oxime+SX, momfluorothrin+SX, monocro ophos+SX, moxidectin+SX, naled+SX, nicotine+SX, nicotine-sulfate+SX, nitenpyram+SX, novaluron+SX, noviflumuron+SX, omethoate+SX, oxamyl+SX, oxydemeton-methyl+SX, parathion+SX, parathion-methyl+SX, permethrin+SX, phenothrin+SX, phenthoate+SX, phorate+SX, phosalone+SX, phosmet+SX, phosphamidon+SX, phosphine+SX, phoxim+SX, pirimicarb+SX, pirimiphos-methyl+SX, potassium cyanide+SX, prallethrin+SX, profenofos+SX, profluthrin+SX, propargite+SX, propetamphos+SX, propoxur+SX, prothiofos+SX, pyflubumide+SX, pymetrozine+SX, pyraclofos+SX, pyrethrins+SX, pyridaben+SX, pyridalyl+SX, pyridaphenthion+SX, pyrifluquinazone+SX, pyrimidifen+SX, pyriminostrobin+SX, pyriprole+SX, pyriproxyfen+SX, quinalphos+SX, resmethrin+SX, rotenone+SX, selamectin+SX, sigma-cypermethrin+SX, silafluofen+SX, sodium borate+SX, sodium cyanide+SX, sodium metaborate+SX, spinetoram+SX, spinosad+SX, spirodiclofen+SX, spiromesifen+SX, spiropidion+SX, spirotetramat+SX, sulfluramid+SX, sulfotep+SX, sulfoxaflor+SX, sulfur+SX, sulfuryl fluoride+SX, tartar emetic+SX, tau-fluvalinate+SX, tebufenozide+SX, tebufenpyrad+SX, tebupirimfos+SX, teflubenzuron+SX, tefluthrin+SX, temephos+SX, terbufos+SX, tetrachlorvinphos+SX, tetradifon+SX, tetramethrin+SX, tetramethylfluthrin+SX, tetraniliprole+SX, theta-cypermethrin+SX, thiacloprid+SX, thiamethoxam+SX, thiocyclam+SX, thiodicarb+SX, thiofanox+SX, thiometon+SX, thiosultap-disodium+SX, thiosultap-monosodium+SX, tioxazafen+SX, tolfenpyrad+SX, tralomethrin+SX, transfluthrin+SX, triazamate+SX, triazophos+SX, trichlorfon+SX, triflumezopyrim+SX, triflumuron+SX, trimethacarb+SX, tyclopyrazoflor+SX, vamidothion+SX, XMC (3,5-dimethylphenyl N-methylcarbamate)+SX, xylylcarb+SX, zeta-cypermethrin+SX, zinc phosphide+SX, 3-bromo-N-[2,4-dichloro-6-(methylcarbamoyl)phenyl]-1-(3,5-dichloropyridin-2-yl)-1H-pyrazole-5-carboxamide (1104384-14-6)+SX, N-[3-chloro-1-(pyridin-3-yl)-1H-pyrazol-4-yl]-N-ethyl-3-(3,3,3-trifluoropropanesulfinyl) propanamide (1477923-37-7)+SX, 2-[3-(ethanesulfonyl) pyridin-2-yl]-5-(trifluoromethanesulfonyl)benzoxazole (1616678-32-0)+SX, 4-[5-(3,5-dichlorophenyl)-5-(trifluoromethyl)-4,5-dihydro-1,2-oxazol-3-yl]-2-methyl-N-(1-oxothietan-3-yl)benzamide (1241050-20-3)+SX, 3-methoxy-N-(5-{5-(trifluoromethyl)-5-[3-(trifluoromethyl)phenyl]-4,5-dihydro-1,2-oxazol-3-yl}indan-1-yl)propanamide (1118626-57-5)+SX, N-[2-bromo-6-chloro-4-(1,1,1,2,3,3,3-heptafluoropropan-2-yl)phenyl]-3-{ethyl [(pyridin-4-yl)carbonyl]amino}-2-methoxybenzamide (1429513-53-0)+SX, N-[2-bromo-6-chloro-4-(1,1,1,2,3,3,3-heptafluoropropan-2-yl)phenyl]-3-[ethyl(4-cyanobenzoyl) amino]-2-methoxybenzamide (1609007-65-9)+SX, N-[2-bromo-6-(difluoromethoxy)-4-(1,1,1,2,3,3,3-heptafluoropropan-2-yl)phenyl]-3-{methyl[(pyridin-4-yl) carbonyl]amino}-2-methoxybenzamide (1630969-78-6)+SX, 1-{2-fluoro-4-methyl-5-[(2,2,2-trifluoroethyl) sulphinyl]phenyl}-3-(trifluoromethyl)-1H-1,2,4-triazole-5-amine (885026-50-6)+SX, BT crop protein Cry1Ab+SX, BT crop protein Cry1Ac±SX, BT crop protein Cry1Fa+SX, BT crop protein Cry1A.105+SX, BT crop protein Cry2Ab+SX, BT crop protein Vip3A+SX, BT crop protein Cry3A+SX, BT crop protein Cry3Ab+SX, BT crop protein Cry3Bb SX, BT crop protein Cry34Ab1/Cry35Ab1+SX, *Adoxophyes arena* granulosis virus+SX, *Anticarsia gemmatalis* multiple nucleopolyhedrovirus (*Anticarsia gemmatalis* mNPV)+SX, *Autographa californica* mNPV FV #11+SX, *Cydia pomonella* granulovirus V15 (*Cydia pomonella* GV V15)+SX, *Cydia pomonella* GV V22+SX, *Cryptophlebia leucotreta* GV+SX, *Dendrolimus punctatus* cypovirus+SX, *Helicoverpa armigera* NPV BV-0003+SX, *Helicoverpa zea* NPV+SX, *Lymantria dispar* NPV+SX, *Mamestra brassicae* NPV+SX, *Mamestra configurata* NPV+SX, *Neodiprion abietis* NPV+SX, *Neodiprion lecontei* NPV+SX, *Neodiprion sertifer* NPV+SX, *Nosema locustae*+SX, *Orgyia pseudotsugata* NPV+SX, *Pieris rapae* GV+SX, *Plodia interpunctella* GV SX, *Spodoptera exigua* mNPV+SX, *Spodoptera littoralis* mNPV+SX, *Spodoptera litura* NPV+SX, *Arthrobotrys dactyloides*+SX, *Bacillus firmus* GB-126+SX, *Bacillus firmus* 1-1582+SX, *Bacillus megaterium*+SX, *Bacillus* sp. AQ175+

SX, *Bacillus* sp. AQ177+SX, *Bacillus* sp. AQ178+SX, *Bacillus sphaericus* 2362+SX, *Bacillus sphaericus* ABTS1743+SX, *Bacillus sphaericus* Serotype H5a5b+SX, *Bacillus thuringiensis* AQ52+SX, *Bacillus thuringiensis* BD #32+SX, *Bacillus thuringiensis* CR-371+SX, *Bacillus thuringiensis* subsp. *Aizawai* ABTS-1857+SX, *Bacillus thuringiensis* subsp. *Aizawai* AM65-52+SX, *Bacillus thuringiensis* subsp. *Aizawai* GC-91+SX, *Bacillus thuringiensis* subsp. *Aizawai* Serotype H-7+SX, *Bacillus thuringiensis* subsp. *Kurstaki* ABTS351+SX, *Bacillus thuringiensis* subsp. *Kurstaki* BMP123+SX, *Bacillus thuringiensis* subsp. *Kurstaki* EG234+SX, *Bacillus thuringiensis* subsp. *Kurstaki* EG7841+SX, *Bacillus thuringiensis* subsp. *Kurstaki* EVB113-19 SX, *Bacillus thuringiensis* subsp. *Kurstaki* F810 SX, *Bacillus thuringiensis* subsp. *Kurstaki* HD-1+SX, *Bacillus thuringiensis* subsp. *Kurstaki* PB54 SX, *Bacillus thuringiensis* subsp. *Kurstaki* SA-11+SX, *Bacillus thuringiensis* subsp. *Kurstaki* SA-12 SX, *Bacillus thuringiensis* subsp. *Tenebriosis* NB176 SX, *Bacillus thuringiensis* subsp. *Thuringiensis* MPPL002+SX, *Bacillus thuringiensis* subsp. *morrisoni*+SX, *Bacillus thuringiensis* var. *colmeri* SX, *Bacillus thuringiensis* var. *darmstadiensis* 24-91+SX, *Bacillus thuringiensis* var. *dendrolimus*+SX, *Bacillus thuringiensis* var. *galleriae*+SX, *Bacillus thuringiensis* var. *israelensis* BMP144+SX, *Bacillus thuringiensis* var. *israelensis* serotype H-14+SX, *Bacillus thuringiensis* var. *japonensis buibui* A396+SX, *Bacillus thuringiensis* var. *san diego*+SX, *Bacillus thuringiensis* var. 7216+SX, *Bacillus thuringiensis* var. *aegypti*+SX, *Bacillus thuringiensis* var. T36+SX, *Beauveria bassiana* ANT-03+SX, *Beauveria bassiana* ATCC74040 SX, *Beauveria bassiana* GHA+SX, *Beauveria brongniartii*+SX, *Burkholderia rinojensis* A396+SX, *Chromobacterium subtsugae* PRAA4-1T+SX, *Dactyllela ellipsospora*+SX, *Dectylaria thaumasia*+SX, *Hirsutella minnesotensis*+SX, *Hirsutella rhossiliensis*+SX, *Hirsutella thompsonii*+SX, *Lagenidium giganteum*+SX, *Lecanicillium lecanii* KV01+SX, *Metarhizium anisopliae* F52 SX, *Metarhizium flavoviride*+SX, *Monacrosporium phymatopagus*+SX, *Paecilomyces fumosoroseus* Apopka97+SX, *Paecilomyces fumosoroseus*+SX, *Paecilomyces lilacinus* 251+SX, *Paecilomyces lilacinus*+SX, *Paecilomyces tenuipes* T1+SX, *Paenibacillus popilliae*+SX, *Pasteuria nishizawae*+SX, *Pasteuria penetrans*+SX, *Pasteuria usgae*+SX, *Pesteuria thoynei*+SX, *Serratia entomophila*+SX, *Verticillium chlamydosporium*+SX, *Verticillium lecani* NCIM1312+SX.

Combination of the present ingredient of the above group (b) and the compound of the present invention:

acibenzolar-S-methyl+SX, aldimorph+SX, ametoctradin+SX, aminopyrifen+SX, amisulbrom+SX, anilazine+SX, azaconazole+SX, azoxystrobin+SX, basic copper chloride+SX, basic copper sulfate+SX, benalaxyl+SX, benalaxyl-M+SX, benodanil+SX, benomyl+SX, benthiavalicarb+SX, benthivalicarb-isopropyl SX, benzovindiflupyr+SX, binapacryl+SX, biphenyl+SX, bitertanol+SX, bixafen+SX, blasticidin-S+SX, boscalid+SX, bromuconazole+SX, bupirimate+SX, captafol+SX, captan SX, carbendazim+SX, carboxin+SX, carpropamid+SX, chinomethionat+SX, chloroneb+SX, chlorothalonil+SX, chlozolinate+SX, colletochlorin B+SX, copper(II) hydroxide+SX, coumoxystrobin+SX, cyazofamid+SX, cyflufenamid+SX, cymoxanil+SX, cyproconazole+SX, cyprodinil SX, dichlobentiazox+SX, dichlofluanid+SX, diclocymet+SX, diclomezine SX, dicloran SX, diethofencarb SX, difenoconazole+SX, diflumetorim+SX, dimethachlone+SX, dimethirimol+SX, dimethomorph+SX, dimoxystrobin+SX, diniconazole+SX, diniconazole-M+SX, dinocap+SX, dipymetitrone+SX, dithianon+SX, dodecylbenzenesulphonic acid bisethylenediamine copper(II) salt+SX, dodemorph+SX, dodine+SX, edifenphos SX, enoxastrobin+SX, epoxiconazole SX, etaconazole SX, ethaboxam+SX, ethirimol+SX, etridiazole+SX, famoxadone+SX, fenamidone+SX, fenaminstrobin+SX, fenarimol+SX, fenbuconazole+SX, fenfuram+SX, fenhexamid+SX, fenoxanil+SX, fenpiclonil SX, fenpicoxamid+SX, fenpropidin+SX, fenpropimorph+SX, fenpyrazamine+SX, fentin acetate+SX, fentin chloride+SX, fentin hydroxide+SX, ferbam+SX, ferimzone+SX, fluazinam+SX, fludioxonil+SX, flufenoxystrobin+SX, fluindapyr+SX, flumorph+SX, fluopicolide+SX, fluoroimide+SX, fluoxastrobin+SX, fluquinconazole+SX, flusilazole+SX, flusulfamide+SX, flutianil SX, flutolanil SX, flutriafol+SX, fluxapyroxad+SX, folpet+SX, fosetyl+SX, fuberidazole+SX, furalaxyl+SX, furametpyr+SX, guazatine+SX, hexaconazole+SX, hymexazole+SX, imazalil+SX, imibenconazole SX, iminoctadine+SX, iodocarb SX, ipconazole+SX, ipfentrifluconazole+SX, iprobenfos+SX, iprodione SX, iprovalicarb+SX, isofetamid SX, isoflucypram+SX, isoprothiolane+SX, isopyrazam+SX, isotianil+SX, kasugamycin+SX, kresoxim-methyl+SX, laminarin+SX, mancozeb+SX, mandestrobin SX, mandipropamid+SX, maneb+SX, mefentrifluconazole+SX, mepanipyrim+SX, mepronil+SX, meptyldinocap SX, metalaxyl SX, metalaxyl-M+SX, metconazole SX, methasulfocarb+SX, metiram+SX, metominostrobin+SX, metrafenone+SX, myclobutanil+SX, naftifine+SX, nuarimol+SX, octhilinone+SX, ofurace+SX, orysastrobin+SX, oxadixyl+SX, oxathiapiprolin+SX, oxolinic acid+SX, oxpoconazole+SX, oxpoconazole fumarate+SX, oxycarboxin+SX, oxytetracycline+SX, pefurazoate+SX, penconazole+SX, pencycuron+SX, penflufen+SX, penthiopyrad+SX, phenamacril SX, phthalide+SX, picarbutrazox SX, picoxystrobin SX, piperalin SX, polyoxins+SX, probenazole SX, prochloraz+SX, procymidone+SX, propamocarb+SX, propiconazole+SX, propineb SX, proquinazid+SX, prothiocarb+SX, prothioconazole+SX, pydiflumetofen+SX, pyraclostrobin+SX, pyrametostrobin+SX, pyraoxystrobin+SX, pyraziflumid+SX, pyrazophos+SX, pyribencarb SX, pyributicarb SX, pyrifenox+SX, pyrimethanil+SX, pyrimorph SX, pyriofenone SX, pyrisoxazole+SX, pyroquilon+SX, quinofumelin+SX, quinoxyfen+SX, quintozene+SX, sedaxane+SX, silthiofam+SX, simeconazole+SX, spiroxamine+SX, streptomycin+SX, sulfur+SX, tebuconazole+SX, tebufloquin+SX, teclofthalam SX, tecnazene SX, terbinafine SX, tetraconazole+SX, thiabendazole+SX, thifluzamide+SX, thiophanate+SX, thiophanate-methyl+SX, thiram+SX, tiadinil+SX, tolclofos-methyl+SX, tolfenpyrad+SX, tolprocarb SX, tolylfluanid SX, triadimefon+SX, triadimenol+SX, triazoxide+SX, triclopyricarb+SX, tricyclazole+SX, tridemorph+SX, trifloxystrobin+SX, triflumizole+SX, triforine SX, triticonazole+SX, validamycin+SX, valifenalate+SX, vinclozolin+SX, zineb+SX, ziram+SX, zoxamide SX, 3-(difluoromethyl)-N-methoxy-1-methyl-N-[(1R)-1-methyl-2-(2,4,6-trichlorophenyl)ethyl]pyrazole-4-carboxamide (1639015-48-7)+SX, 3-(difluoromethyl)-N-methoxy-1-methyl-N-[(1S)-1-methyl-2-(2,4,6-trichlorophenyl)ethyl]pyrazole-4-carboxamide (1639015-49-8)+SX, 3-(difluoromethyl)-1-methyl-N-(1,1,3-trimethylindan-4-yl)pyrazole-4-carboxamide (141573-94-6)+SX, 3-(difluoromethyl)-1-methyl-N-[(3R)-1,1,3-trimethylindan-4-yl]pyrazole-4-carboxamide (1352994-67-2) SX, 3-(difluoromethyl)-N-[(3R)-7-fluoro-1,1,3-trimethylindan-4-yl]-1-methylpyrazole-4-carboxamide (1513466-73-3)+SX, 3-chloro-5-phenyl-6-methyl-4-(2,6-difluorophenyl) pyridazine (1358061-55-8)+SX, N'-[4-({3-[(4-chlorophenyl)methyl]-1,2,4-thiadiazol-5-yl}oxy)-2,5-dimethylphenyl]-N-ethyl-N-methylmethanimidamide (1202781-91-6) SX, 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl-methanesulfonate (1360819-11-9) SX, 4-(2-bromo-4-fluorophenyl)-N-(2-chloro-6-fluorophenyl)-1,3-dimethyl-1H-pyrazol-5-amine (1362477-26-6) SX, 2,2-dimethyl-9-fluoro-5-(quinolin-3-yl)-2,3-dihydrobenz[f][1,4]oxazepine (1207749-50-5)+SX, 2-[6-(3-fluoro-4-methoxyphenyl)-5-methylpyridin-2-yl]quinazoline (1257056-97-5)+SX, 5-fluoro-2-[(4-methylphenyl)methoxy]-4-pyrimidinamine (1174376-25-0)+SX, 5-fluoro-4-imino-3-methyl-1-tosyl-3,4-dihydropyrimidin-2(1H)-one (1616664-98-2)+SX, N'-(2,5-dimethyl-4-phenoxyphenyl)-N-ethyl-N-methylmethanimidamide (1052688-31-9) SX, N'-{4-[(4,5-dichlorothiazol-2-yl)oxy]-2,5-dimethylphenyl}-N-ethyl-N-methylmethanimidamide (929908-57-6)+SX, ethyl (2Z)-3-amino-2-cyano-3-phenylacrylate (39491-78-6)+SX, N-[(2-chlorothiazol-5-yl)methyl]-N-ethyl-6-methoxy-3-nitropyridin-2-amine (1446247-98-8)+SX, 1-[2-({[1-(4-chlorophenyl)-1H-pyrazol-3-yl]oxy}methyl)-3-methylphenyl]-4-methyl-5-oxo-4,5-dihydro-1H-tetrazole (1472649-01-6)+SX, α-[3-(4-chloro-2-fluorophenyl)-5-(2,4-difluorophenyl)-4-isoxazolyl]-3-pyridinemethanol (1229605-96-2)+SX, (αS)-[3-(4-chloro-2-fluorophenyl)-5-(2,4-difluorophenyl)-4-isoxazolyl]-3-pyridinemethanol (1229606-46-5)+SX, (αR)-[3-(4-chloro-2-fluorophenyl)-5-(2,4-difluorophenyl)-4-isoxazolyl]-3-pyridinemethanol (1229606-02-3) SX, 2-{[3-(2-chlorophenyl)-2-(2,4-difluorophenyl)oxiran-2-yl]methyl}-2,4-dihydro-3H-1,2,4-triazole-3-thione (1342260-19-8)+SX, 2-{[(2R,3S)-3-(2-chlorophenyl)-2-(2,4-difluorophenyl)oxiran-2-yl]methyl}-2,4-dihydro-3H-1,2,4-triazole-3-thione (1638897-70-7)+SX, 2-{[(2S,3R)-3-(2-chlorophenyl)-2-(2,4-difluorophenyl)oxiran-2-yl]methyl}-2,4-dihydro-3H-1,2,4-triazole-3-thione (1638897-71-8) SX, 2-{[(2R,3R)-3-(2-chlorophenyl)-2-(2,4-difluorophenyl)oxiran-2-yl]methyl}-2,4-dihydro-3H-1,2,4-triazole-3-thione (1638897-72-9)+SX, 2-{[(2S,3S)-3-(2-chlorophenyl)-2-(2,4-difluorophenyl)oxiran-2-yl]methyl}-2,4-dihydro-3H-1,2,4-triazole-3-thione (1638897-73-0) SX, 1-{[3-(2-chlorophenyl)-2-(2,4-difluorophenyl)oxiran-2-yl]methyl}-1H-1,2,4-triazol-5-yl thiocyanate (1342260-26-7)+SX, 1-{[(2R,3S)-3-(2-chlorophenyl)-2-(2,4-difluorophenyl)oxiran-2-yl]methyl}-1H-1,2,4-triazol-5-yl thiocyanate (1638897-82-1) SX, 1-{[(2S,3R)-3-(2-chlorophenyl)-2-(2,4-difluorophenyl)oxiran-2-yl]methyl}-1H-1,2,4-triazol-5-yl thiocyanate (1638897-84-3)+SX, 1-{[(2R,3R)-3-(2-chlorophenyl)-2-(2,4-difluorophenyl)oxiran-2-yl]methyl}-1H-1,2,4-triazol-5-yl thiocyanate (1638897-86-5)+SX, 1-{[(2S,3S)-3-(2-chlorophenyl)-2-(2,4-difluorophenyl)oxiran-2-yl]methyl}-1H-1,2,4-triazol-5-yl thiocyanate (1638897-89-8)+SX, 5-(4-chlorobenzyl)-2-(chloromethyl)-2-methyl-1-(1H-1,2,4-triazol-1-ylmethyl)cyclopentanol (1394057-11-4)+SX, (1R,2S,5S)-5-(4-chlorobenzyl)-2-chloromethyl-2-methyl-1-(1H-1,2,4-triazol-1-ylmethyl)cyclopentanol (1801930-06-2)+SX, (1S,2R,5R)-5-(4-chlorobenzyl)-2-chloromethyl-2-methyl-1-(1H-1,2,4-triazol-1-ylmethyl)cyclopentanol (1801930-07-3) SX, (1R,2R,5R)-5-(4-chlorobenzyl)-2-chloromethyl-2-methyl-1-(1H-1,2,4-triazol-1-ylmethyl)cyclopentanol (1801919-53-8)+SX, (1S,2S,5S)-5-(4-chlorobenzyl)-2-chloromethyl-2-methyl-1-(1H-1,2,4-triazol-1-ylmethyl)cyclopentanol (1801919-54-9)+SX, (1R,2R,5S)-5-(4-chlorobenzyl)-2-chloromethyl-2-methyl-1-(1H-1,2,4-triazol-1-ylmethyl)cyclopentanol (1801919-55-0) SX, (1S,2S,5R)-5-(4-chlorobenzyl)-2-chloromethyl-2-methyl-1-(1H-1,2,4-triazol-1-ylmethyl)cyclopentanol (1801919-56-1)+SX, (1R,2S,5R)-5-(4-chlorobenzyl)-2-chloromethyl-2-methyl-1-(1H-1,2,4-triazol-1-ylmethyl)cyclopentanol (1801919-57-2)+SX, (1S,2R,5S)-5-(4-chlorobenzyl)-2-chloromethyl-2-methyl-1-(1H-1,2,4-triazol-1-ylmethyl)cyclopentanol (1801919-58-3)+SX, methyl 3-[(4-chlorophenyl)methyl]-2-hydroxy-1-methyl-2-(1H-1,2,4-triazol-1-ylmethyl)cyclopentane carboxylate (1791398-02-1)+SX, methyl (1R,2S,3S)-3-[(4-chlorophenyl)methyl]-2-hydroxy-1-methyl-2-(1H-1,2,4-triazol-1-ylmethyl) cyclopentane carboxylate SX, methyl (1S,2R,3R)-3-[(4-chlorophenyl)methyl]-2-hydroxy-1-methyl-2-(1H-1,2,4-triazol-1-ylmethyl)cyclopentane carboxylate SX, methyl (1R,2R,3R)-3-[(4-chlorophenyl)methyl]-2-hydroxy-1-methyl-2-(1H-1,2,4-triazol-1-ylmethyl)cyclopentane carboxylate+SX, methyl (1S,2S,3S)-3-[(4-chlorophenyl)methyl]-2-hydroxy-1-methyl-2-(1H-1,2,4-triazol-1-ylmethyl)cyclopentane carboxylate SX, methyl (1R,2R,3S)-3-[(4-chlorophenyl)methyl]-2-hydroxy-1-methyl-2-(1H-1,2,4-triazol-1-ylmethyl)cyclopentane carboxylate SX, methyl (1S,2S,3R)-3-[(4-chlorophenyl)methyl]-2-hydroxy-1-methyl-2-(1H-1,2,4-triazol-1-ylmethyl)cyclopentane carboxylate+SX, methyl (1R,2S,3R)-3-[(4-chlorophenyl)methyl]-2-hydroxy-1-methyl-2-(1H-1,2,4-triazol-1-ylmethyl)cyclopentane carboxylate SX, methyl (1S,2R,3S)-3-[(4-chlorophenyl)methyl]-2-hydroxy-1-methyl-2-(1H-1,2,4-triazol-1-ylmethyl)cyclopentane carboxylate+SX, chloromethyl-5-(4-fluorobenzyl)-2-methyl-1-(1H-1,2,4-triazol-1-ylmethyl)cyclopentanol (1394057-13-6)+SX, (1R,2S,5S)-2-chloromethyl-5-(4-fluorobenzyl)-2-methyl-1-(1H-1,2,4-triazol-1-ylmethyl)cyclopentanol (1801930-08-4)+SX, (1S,2R,5R)-2-chloromethyl-5-(4-fluorobenzyl)-2-methyl-1-(1H-1,2,4-triazol-1-ylmethyl)cyclopentanol (1801930-09-5)+SX, (1R,2R,5R)-2-chloromethyl-5-(4-fluorobenzyl)-2-methyl-1-(1H-1,2,4-triazol-1-ylmethyl)cyclopentanol (1638898-08-4) SX, (1S,2S,5S)-2-chloromethyl-5-(4-fluorobenzyl)-2-methyl-1-(1H-1,2,4-triazol-1-ylmethyl)cyclopentanol (1638898-10-8)+SX, (1R,2R,5S)-2-chloromethyl-5-(4-fluorobenzyl)-2-methyl-1-(1H-1,2,4-triazol-1-ylmethyl)cyclopentanol (1638898-13-1) SX, (1S,2S,5R)-2-chloromethyl-5-(4-fluorobenzyl)-2-methyl-1-(1H-1,2,4-triazol-1-ylmethyl)cyclopentanol (1638898-16-4)+SX, (1R,2S,5R)-2-chloromethyl-5-(4-fluorobenzyl)-2-methyl-1-(1H-1,2,4-triazol-1-ylmethyl)cyclopentanol (1638898-20-0)+SX, (1S,2R,5S)-2-chloromethyl-5-(4-fluorobenzyl)-2-methyl-1-(1H-1,2,4-triazol-1-ylmethyl)cyclopentanol (1638898-24-4) SX, (R)-2-[2-chloro-4-(4-chlorophenoxy)phenyl]-1-(1,2,4-triazol-1-yl)pent-3-yn-2-ol (1801919-59-4) SX, (R)-2-[4-(4-chlorophenoxy)-2-(trifluoromethyl)phenyl]-1-(1,2,4-triazol-1-yl)propan-2-ol (1616236-94-2) SX, (R)-1-[4-(4-chlorophenoxy)-2-(trifluoromethyl)phenyl]-1-cyclopropyl-2-(1,2,4-triazol-1-yl)ethanol (1801919-60-7)+SX, (R)-2-[4-(4-chlorophenoxy)-2-(trifluoromethyl)phenyl]-3-methyl-1-(1,2,4-triazol-1-yl)butan-2-ol (1801919-61-8)+SX, 3-[5-(4-Chlorophenyl)-2,3-dimethyl-1,2-oxazolidin-3-yl]pyridine (847749-37-5)+SX, *Agrobacterium radiobactor* K1026+SX, *Agrobacterium radiobactor* K84+SX, *Bacillus amyloliquefaciens* AT332+SX, *Bacillus amyloliquefaciens* B3 SX, *Bacillus amyloliquefaciens* D747+SX, *Bacillus amyloliquefaciens* FZB24+SX, *Bacillus amyloliquefaciens* FZB42+SX, *Bacillus amyloliquefaciens* IN937a+SX, *Bacillus amyloliquefaciens* MBI600+SX, *Bacillus amyloliquefaciens* PTA-4838 SX, *Bacillus amyloliquefaciens* QST713 SX, *Bacillus licheniformis* HB-2+SX, *Bacillus licheniformis* SB3086+SX, *Bacillus pumilus* AQ717+SX, *Bacillus pumilus* BUF-33+SX, *Bacillus pumilus* GB34+SX, *Bacillus pumilus* QST2808+SX, *Bacillus simplex* CGF2856+SX, *Bacillus subtilis* AQ153+SX, *Bacillus subtilis* AQ743+SX, *Bacillus subtilis* D747+SX, *Bacillus subtilis* DB101+SX, *Bacillus*

*subtilis* GB03+SX, *Bacillus subtilis* HAI0404+SX, *Bacillus subtilis* IAB/BS03+SX, *Bacillus subtilis* MBI600+SX, *Bacillus subtilis* QST30002/AQ30002+SX, *Bacillus subtilis* QST30004/AQ30004+SX, *Bacillus subtilis* QST713+SX, *Bacillus subtilis* QST714+SX, *Bacillus subtilis* var. *Amyloliquefaciens* FZB24 etc.+SX, *Bacillus subtilis* Y1336+SX, *Burkholderia cepacia*+SX, *Candida oleophila* O+SX, *Candida saitoana*+SX, *Chaetomium cupreum*+SX, *Clonostachys rosea*+SX, *Coniothyrium minitans* CGMCC8325+SX, *Coniothyrium minitans* CON/M/91-8+ SX, *cryptococcus albidus*+SX, *Erwinia carotovora* CGE234M403+SX, *Fusarium oxysporum* Fo47+SX, *Gliocladium catenulatum* J1446+SX, *Paenibacillus polymyxa* AC-1+SX, *Paenibacillus polymyxa* BS-0105+SX, *Pantoea agglomerans* E325+SX, *Phlebiopsis gigantea*+SX, *Pseudomonas aureofaciens* TX-1+SX, *Pseudomonas chlororaphis* 63-28 SX, *Pseudomonas chlororaphis* MA342+ SX, *Pseudomonas fluorescens* 1629RS+SX, *Pseudomonas fluorescens* A506+SX, *Pseudomonas fluorescens* CL145A+ SX, *Pseudomonas fluorescens* G7090+SX, *Pseudomonas fluorescens* PF-A22UL+SX, *Pseudomonas syringae* 742RS+SX, *Pseudomonas syringae* MA-4+SX, *Pseudozyma flocculosa* PF-A22UL+SX, *Pseudomonas rhodesiae* HAI-0804+SX, *pythium oligandrum* DV74+SX, *Streptomyces griseoviridis* K61+SX, *Streptomyces lydicus* WYCD108US+SX, *Streptomyces lydicus* WYEC108+SX, *Talaromyces flavus* SAY-Y-94-01+SX, *Talaromyces flavus* SAY-Y-94-01+SX, *Trichoderma asperellum* ICC012+SX, *Trichoderma asperellum* T34+SX, *Trichoderma atroviride* CNCM 1-1237+SX, *Trichoderma atroviride* SC1+SX, *Trichoderma atroviride* SKT-1+SX, *Trichoderma harzianum*+SX, *Trichoderma harzianum* DB104+SX, *Trichoderma harzianum* DSM 14944+SX, *Trichoderma harzianum* ESALQ-1303+SX, *Trichoderma harzianum* ESALQ-1306+SX, *Trichoderma harzianum* IIHR-Th-2+ SX, *Trichoderma harzianum* kd+SX, *Trichoderma harzianum* MO1+SX, *Trichoderma harzianum* SF+SX, *Trichoderma harzianum* T39+SX, *Trichoderma polysporum* EVII 206039+SX, *Trichoderma stromaticum*+SX, *Trichoderma viride* GL-21+SX, *Variovorax paradoxus* CGF4526+SX, Harpin protein+SX.

Combination of the present ingredient of the above group (c) and the compound of the present invention:

1-methylcyclopropene+SX, 2,3,5-triiodobenzoic acid+ SX, IAA ((1H-indol-3-yl)acetic acid)+SX, IBA (4-(1H-indol-3-yl)butyric acid) SX, MCPA (2-(4-chloro-2-methylphenoxy)acetic acid)+SX, MCPB (4-(4-chloro-2-methylphenoxy)butyric acid) SX, 4-CPA (4-chlorophenoxyacetic acid) SX, 5-aminolevulinic acid hydrochloride+SX, 6-benzylaminopurine+SX, abscisic acid+SX, AVG (aminoethoxyvinylglycine)+SX, ancymidol+SX, butralin+SX, calcium carbonate+SX, calcium chloride+SX, calcium formate+SX, calcium peroxide+SX, calcium polysulfide+SX, calcium sulfate+SX, chlormequatchloride+SX, chlorpropham+SX, choline chloride+SX, cloprop+SX, cyanamide+SX, cyclanilide+SX, daminozide+ SX, decan-1-ol+SX, dichlorprop+SX, dikegulac+SX, dimethipin+SX, diquat+SX, ethephon SX, ethychlozate+SX, flumetralin+SX, flurprimidol+SX, forchlorfenuron+SX, Gibberellin A+SX, Gibberellin A3+SX, inabenfide+SX, Kinetin+SX, maleic hydrazide+SX, mefluidide+SX, mepiquat-chloride SX, oxidized glutathione SX, pacrobutrazol SX, pendimethalin SX, prohexandione-calcium+SX, prohydrojasmon+SX, pyraflufen-ethyl+SX, sintofen+SX, sodium 1-naphthaleneacetate+SX, sodium cyanate+SX, streptmycin+SX, thidiazuron SX, triapenthenol+SX, Tribufos+SX, trinexapac-ethyl+SX, uniconazole-P+SX, 2-(naphthalene-1-yl)acetamide+SX, [4-oxo-4-(2-phenylethyl)amino]butyric acid+SX, methyl 5-(trifluoromethyl)benzo[b]thiophene-2-carboxylate+SX, 3-[(6-chloro-4-phenylquinazolin-2-yl)amino]-1-propanol+SX, *Glomus* spp.+SX, *Glomus intraradices*+SX, *Glomus mosseae* SX, *Glomus aggregatum*+SX, *Glomus etunicatum*+SX, *Bradyrhizobium elkani*+SX, *Bradyrhizobium japonicum*+SX, *Bradyrhizobium lupini* SX, *Rhizobium leguminosarum* bv. *trifolii*+SX, *Rhizobium leguminosarum* bv. *phaseoli*+SX, *Rhizobium leguminosarum* bv. *viciae*+SX, *Sinorhizobium meliloti*+SX, *Rhizobium* spp.+ SX.

Combination of the present ingredient of the above group (d) and the compound of the present invention:

allidochlor+SX, benoxacor+SX, cloquintocet+SX, cloquintocet-mexyl+SX, cyometrinil+SX, cyprosulfamide+ SX, dichlormid+SX, dicyclonone+SX, dimepiperate+SX, disulfoton SX, dymron SX, fenchlorazole SX, fenchlorazole-ethyl+SX, fenclorim+SX, flurazole+SX, furilazole+ SX, fluxofenim+SX, Hexim+SX, isoxadifen+SX, isoxadifen-ethyl SX, mecoprop+SX, mefenpyr+SX, mefenpyr-ethyl+SX, mefenpyr-diethyl+SX, mephenaLe+SX, metcamifen+SX, oxabetrinil+SX, 1,8-naphthalic anhydride+ SX, 1,8-octamethylene diamine SX, AD-67 (4-(dichloroacetyl)-1-oxa-4-azaspiro[4.5]decane)+SX, CL-304415 (4-carboxy-3,4-dihydro-2H-1-benzopyran-4-acetic acid)+SX, CSB (1-bromo-4-[(chloromethyl)sulfonyl]benzene)+SX, DKA-24 (2,2-dichloro-N-[2-oxo-2-(2-propenylamino)ethyl]-N-(2-propenyl)acetamide) SX, MG191 (2-(dichloromethyl)-2-methyl-1,3-dioxolane)+SX, MG-838 (2-propenyl 1-oxa-4-azaspiro[4.5]decane-4-carbodithioate)+SX, PPG-1292 (2,2-dichloro-N-(1,3-dioxan-2-ylmethyl)-N-(2-propenyl)acetamide)+SX, R-28725 (3-(dichloroacetyl)-2,2-dimethyl-1,3-oxazolidine)+SX, R-29148 (3-(dichloroacetyl)-2,2,5-trimethyl-1,3-oxazolidine) SX, TI-35 (1-(dichloroacetyl)azepane)+SX.

Combination of the present ingredient of the above group (e) and the compound of the present invention:

1-dodecyl-1H-imidazole+SX, N-(2-ethylhexyl)-8,9,10-trinorborn-5-ene-2,3-dicarboximide+SX, bucarpolate+SX, N,N-dibutyl-4-chlorobenzenesulfonamide+SX, dietholate+ SX, diethylmaleate+SX, piperonyl butoxide+SX, piperonyl cyclonene+SX, piprotal+SX, propyl isome+SX, safroxan+ SX, sesamex+SX, sesamolin+SX, sulfoxide+SX, Verbutin+ SX, DMC (1,1-bis(4-chlorophenyl)ethanol)+SX, FDMC (1,1-bis(4-chlorophenyl)-2,2,2-trifluoroethanol)+SX, ETN (1,2-epoxy-1,2,3,4-tetrahydronaphthalene)+SX, ETP (1,1,1-trichloro-2,3-expoxypropane)+SX, PSCP (phenylsaligenin cyclic phosphate) SX, TBPT (S,S,S-tributyl phosphorotrithioate)+SX, TPP (triphenyl phosphate)+SX.

A ratio of the compound of the present invention to the present ingredient includes, but not limited thereto, as a ratio by weight (the compound of the present invention:the present ingredient) 1000:1 to 1:1000, 500:1 to 1:500, 100:1 to 1:100, 50:1 to 1:50, 20:1 to 1:20, 10:1 to 1:10, 3:1 to 1:3, 1:1 to 1:500, 1:1 to 1:100, 1:1 to 1:50, 1:1 to 1:20, 1:1 to 1:10, and the others.

Examples of the pest on which the compound of the present invention has control efficacies include harmful arthropods such as harmful insects and harmful mites. Specific examples of the pest include, but are not limited to, the followings.

Hemiptera:

from the family Delphacidae, for example, small brown planthopper (*Laodelphax striatellus*), brown planthopper (*Nilaparvata lugens*), white-backed planthopper (*Sogatella furcifera*), corn planthopper (*Peregrinus maidis*), cereal leafhopper (*Javesella pellucida*), sugarcane leafhopper (*Perkinsiella saccharicida*), and *Tagosodes orizicolus*;

from the family Cicadellidae, for example, green rice leafhopper (*Nephotettix cincticeps*), green paddy leafhopper (*Nephotettix virescens*), rice leafhopper (*Nephotettix nigropictus*), zigzag-striped leafhopper (*Recilia dorsalis*), tea green leafhopper (*Empoasca onukii*), potato leafhopper (*Empoasca fabae*), corn leafhopper (*Dalbulus maidis*), and rice leafhopper (*Cofana spectra*);

from the family Cercopidae, for example, *Mahanarva posticata* and *Mahanarva fimbriolata*;

from the family Aphididae, for example, bean aphid (*Aphis fabae*), soybean aphid (*Aphis glycines*), cotton aphid (*Aphis gossypii*), green apple aphid (*Aphis pomi*), apple aphid (*Aphis spiraecola*), green peach aphid (*Myzus persicae*), leaf-curling plum aphid (*Brachycaudus helichrysi*), cabbage aphid (*Brevicoryne brassicae*), Rosy apple aphid (*Dysaphis plantaginea*), false cabbage aphid (*Lipaphis erysimi*), potato aphid (*Macrosiphum euphorbiae*), foxglove aphid (*Aulacorthum solani*), lettuce aphid (*Nasonovia ribisnigri*), grain aphid (*Rhopalosiphum padi*), corn aphid (*Rhopalosiphum maidis*), brown citrus aphid (*Toxoptera citricida*), mealy plum aphid (*Hyalopterus pruni*), cane aphid (*Melanaphis sacchari*), black rice root aphid (*Tetraneura nigriabdominalis*), sugarcane cottony aphid (*Ceratovacuna lanigera*), and apple woolly aphid (*Eriosoma lanigerum*);

from the family Phylloxeridae, for example, grapevine phylloxera (*Daktulosphaira vitifoliae*), Pecan phylloxera (*Phylloxera devastatrix*), Pecan leaf phylloxera (*Phylloxera notabilis*), and Southern pecan leaf phylloxera (*Phylloxera russelae*);

from the family Adelgidae, for example, hemlock woolly aphid (*Adelges tsugae*), *Adelges piceae*, and *Aphrastasia pectinatae*;

from the family Pentatomidae, for example, black rice bug (*Scotinophara lurida*), Malayan rice black bug (*Scotinophara coarctata*), common green stink bug (*Nezara antennata*), white-spotted spined bug (*Eysarcoris aeneus*), lewis spined bug (*Eysarcoris lewisi*), white-spotted bug (*Eysarcoris ventralis*), *Eysarcoris annamita*, brown marmorated stink bug (*Halyomorpha halys*), green plant bug (*Nezara viridula*), Brown stink bug (*Euschistus heros*), Red banded stink bug (*Piezodorus guildinii*), *Oebalus pugnax*, and *Dichelops melacanthus*;

from the family Cydnidae, for example, Burrower brown bug (*Scaptocoris castanea*);

from the family Alydidae, for example, bean bug (*Riptortus pedestris*), corbett rice bug (*Leptocorisa chinensis*), and rice bug (*Leptocorisa acuta*);

from the family Coreidae, for example, Cletus punctiger, and Australian leaf-footed bug (*Leptoglossus australis*);

from the family Lygaeidae, for example, oriental chinch bug (*Caverelius saccharivorus*), seed bug (*Togo hemipterus*), and chinch bug (*Blissus leucopterus*);

from the family Miridae, for example, rice leaf bug (*Trigonotylus caelestialium*), sorghum plant bug (*Stenotus rubrovittatus*), wheat leaf bug (*Stenodema calcarata*), and American tarnished plant bug (*Lygus lineolaris*);

from the family Aleyrodidae, for example, greenhouse whitefly (*Trialeurodes vaporariorum*), tobacco whitefly (*Bemisia tabaci*), citrus whitefly (*Dialeurodes citri*), citrus spiny whitefly (*Aleurocanthus spiniferus*), tea spiny whitefly (*Aleurocanthus camelliae*), and *Pealius euryae*;

from the family Diaspididae, for example, *Abgrallaspis cyanophylli*, red scale (*Aonidiella aurantii*), San José scale (*Diaspidiotus perniciosus*), white peach scale (*Pseudaulacaspis pentagona*), arrowhead scale (*Unaspis yanonensis*), and citrus snow scale (*Unaspis citri*);

from the family Coccidae, for example, pink wax scale (*Ceroplastes rubens*);

from the family Margarodidae, for example, fluted scale (*Icerya purchasi*) and seychelles fluted scale (*Icerya seychellarum*);

from the family Pseudococcidae, for example, solanum mealybug (*Phenacoccus solani*), cotton mealybug (*Phenacoccus solenopsis*), Japanese mealybug (*Planococcus kraunhiae*), white peach scale (*Pseudococcus comstocki*), citrus mealybug (*Planococcus citri*), currant mealybug (*Pseudococcus calceolariae*), long-tailed mealybug (*Pseudococcus longispinus*), and tuttle mealybug (*Brevennia rehi*);

from the family Psyllidae, for example, citrus psylla (*Diaphorina citri*), two-spotted citrus psyllid (*Trioza erytreae*), pear sucker (*Cacopsylla pyrisuga*), *Cacopsylla chinensis*, potato psyllid (*Bactericera cockerelli*), and Pear psylla (*Cacopsylla pyricola*);

from the family Tingidae, for example, sycamore lace bug (*Corythucha ciliata*), aster tingid (*Corythucha marmorata*), Japanese pear lace bug (*Stephanitis nashi*), and azalea lace bug (*Stephanitis pyrioides*);

from the family Cimicidae, for example, common bed bug (*Cimex lectularius*);

from the family Cicadidae, for example, Giant Cicada (*Quesada gigas*);

and the others.

Lepidoptera:

from the family Crambidae, for example, rice stem borer (*Chilo suppressalis*), Darkheaded stem borer (*Chilo polychrysus*), White stem borer (*Scirpophaga innotata*), yellow paddy borer (*Scirpophaga incertulas*), *Rupela albina*, rice leaf roller (*Cnaphalocrocis medinalis*), *Marasmia patnalis*, rice leaf roller (*Marasmia exigua*), cotton leaf roller (*Notarcha derogata*), corn borer (*Ostrinia furnacalis*), European corn borer (*Ostrinia nubilalis*), cabbage webworm (*Hellula undalis*), grape leafroller (*Herpetogramma luctuosale*), bluegrass webworm (*Pediasia teterrellus*), rice case-worm (*Nymphula depunctalis*), and Sugarcane borer (*Diatraea saccharalis*);

from the family Pyralidae, for example, lesser cornstalk borer (*Elasmopalpus lignosellus*) and mealworm moth (*Plodia interpunctella*);

from the family Noctuidae, for example, cotton worm (*Spodoptera litura*), beet armyworm (*Spodoptera exigua*), rice armyworm (*Mythimna separata*), cabbage moth (*Mamestra brassicae*), pink borer (*Sesamia inferens*), grass armyworm (*Spodoptera mauritia*), green rice caterpillar (*Naranga aenescens*), *Spodoptera frugiperda*, true armyworm (*Spodoptera exempta*), black cutworm (*Agrotis ipsilon*), beet worm (*Autographa nigrisigna*), rice looper (*Plasia festucae*), Soybean looper (*Chrysodeixis includens*), *Trichoplusia* spp., *Heliothis* spp. (such as tobacco budworm (*Heliothis virescens*)), *Helicoverpa* spp. (such as tobacco budworm (*Helicoverpa armigera*) and corn earworm (*Helicoverpa zea*)), Velvetbean caterpillar (*Anticarsia gemmatalis*), Cotton leafworm (*Alabama argillacea*), and Hop vine borer (*Hydraecia immanis*);

from the family Pieridae, for example, common cabbage worm (*Pieris rapae*);

from the family Tortricidae, for example, oriental fruit moth (*Grapholita molesta*), *Grapholita dimorpha*, soybean moth (*Leguminivora glycinivorella*), *Matsumuraeses azukivora*, summer fruit tortrix (*Adoxophyes orana fasciata*), smaller tea tortrix (*Adoxophyes honmai*), Japanese tea tortrix (*Homona magnanima*), apple tortrix (*Archips fuscocupreanus*), codling moth (*Cydia pomonella*), sugarcane shoot borer (*Tetramoera schistaceana*), Bean Shoot Borer (*Epinotia aporema*), and Citrus fruit borer (*Ecdytolopha aurantiana*);

from the family Gracillariidae, for example, tea leaf roller (*Caloptilia theivora*) and Asiatic apple leaf miner (*Phyllonorycter ringoniella*);

from the family Carposinidae, for example, peach fruit moth (*Carposina sasakii*);

from the family Lyonetiidae, for example, Coffee Leaf miner (*Leucoptera coffeella*), peach leaf miner (*Lyonetia clerkella*), and *Lyonetia prunifoliella*;

from the family Lymantriidae, for example, *Lymantria* spp. (such as gypsy moth (*Lymantria dispar*)) and *Euproctis* spp. (such as tea lymantriid (*Euproctis pseudoconspersa*));

from the family Plutellidae, for example, diamondback moth (*Plutella xylostella*);

from the family Gelechiidae, for example, peach worm (*Anarsia lineatella*), sweetpotato leaf folder (*Helcystogramma triannulella*), pink bollworm (*Pectinophora gossypiella*), potato moth (*Phthorimaea operculella*), and *Tuta absoluta*;

from the family Arctiidae, for example, American white moth (*Hyphantria cunea*);

from the family Castniidae, for example, Giant Sugarcane borer (*Telchin licus*);

from the family Cossidae, for example, *Cossus insularis*;

from the family Geometridae, for example, *Ascotis selenaria*;

from the family Limacodidae, for example, blue-striped nettle grub (*Parasa lepida*);

from the family Stathmopodidae, for example, persimmon fruit moth (*Stathmopoda masinissa*);

from the family Sphingidae, for example, tobacco hornworm (*Acherontia lachesis*);

from the family Sesiidae, for example, *Nokona feralis*;

from the family Hesperiidae, for example, rice skipper (*Parnara guttata*);

and the others.

Thysanoptera:

from the family Thripidae, for example, western flower thrips (*Frankliniella occidentalis*), oriental thrips (*Thrips palmi*), yellow tea thrips (*Scirtothrips dorsalis*), onion thrips (*Thrips tabaci*), eastern flower thrips (*Frankliniella intonsa*), rice thrips (*Stenchaetothrips biformis*), and *Echinothrips americanus*;

from the family Phlaeothripidae, for example, aculeated rice thrips (*Haplothrips aculeates*);

and the others.

Diptera:

from the family Anthomyiidae, for example, seedcorn maggot (*Delia platura*) and onion maggot (*Delia antiqua*);

from the family Ulidiidae, for example, sugarbeet root maggot (*Tetanops myopaeformis*);

from the family Agromyzidae, for example, rice leaf miner (*Agromyza oryzae*), tomato leaf miner (*Liriomyza sativae*), chrysanthemum leaf miner (*Liriomyza trifolii*), and pea leafminer (*Chromatomyia horticola*);

from the family Chloropidae, for example, rice stem maggot (*Chlorops oryzae*);

from the family Tephritidae, for example, melon fly (*Bactrocera cucurbitae*), oriental fruit fly (*Bactrocera dorsalis*), Malaysian fruit fly (*Bactrocera latifrons*), olive fruit fly (*Bactrocera oleae*), Queensland fruit fly (*Bactrocera tryoni*), and Mediterranean fruit fly (*Ceratitis capitata*);

from the family Ephydridae, for example, smaller rice leaf miner (*Hydrellia griseola*), whorl maggot (*Hydrellia philippina*), and paddy stem maggot (*Hydrellia sasakii*);

from the family Drosophilidae, for example, cherry drosophila (*Drosophila suzukii*);

from the family Phoridae, for example, *Megaselia spiracularis*;

from the family Psychodidae, for example, *Clogmia albipunctata*;

from the family Sciaridae, for example, *Bradysia difformis*;

from the family Cecidomyiidae, for example, hessian fly (*Mayetiola destructor*), and paddy gall fly (*Orseolia oryzae*);

from the family Diopsidae, for example, *Diopsis macrophthalma*;

from the family Tipulidae, for example, rice crane fly (*Tipula aino*), Common cranefly (*Tipula cleracea*), and European cranefly (*Tipula paludosa*);

and the others.

Coleoptera:

from the family Chrysomelidae, for example, western corn rootworm (*Diabrotica virgifera virgifera*), southern corn rootworm (*Diabrotica undecimpunctata howardi*), northern corn rootworm (*Diabrotica barberi*), Mexican corn rootworm (*Diabrotica virgifera zeae*), banded cucumber beetle (*Diabrotica balteata*), Cucurbit beetle (*Diabrotica speciosa*), bean leaf beetle (*Cerotoma trifurcata*), barley leaf beetle (*Oulema melanopus*), cucurbit leaf beetle (*Aulacophora femoralis*), striped flea beetle (*Phyllotreta striolata*), Cabbage flea beetle (*Phyllotreta cruciferae*), Western black flea beetle (*Phyllotreta pusilla*), Cabbage stem flea beetle (*Psylliodes chrysocephala*), Colorado potato beetle (*Leptinotarsa decemlineata*), rice leaf beetle (*Oulema oryzae*), grape colaspis (*Colaspis brunnea*), corn flea beetle (*Chaetocnema pulicaria*), sweet-potato flea beetle (*Chaetocnema confinis*), potato flea beetle (*Epitrix cucumeris*), rice leaf beetle (*Dicladispa armigera*), southern corn leaf beetle (*Myochrous denticollis*), *Laccoptera quadrimaculata*, and tobacco flea beetle (*Epitrix hirtipennis*);

from the family Carabidae, for example, Seedcorn beetle (*Stenolophus lecontei*) and Slender seedcorn beetle (*Clivina impressifrons*);

from the family Scarabaeidae, for example, cupreus chafer (*Anomala cuprea*), soybean beetle (*Anomala rufocuprea*), *Anomala albopilosa*, Japanese beetle (*Popillia japonica*), yellowish elongate chafer (*Heptophylla picea*), European Chafer (*Rhizotrogus majalis*), *Tomarus gibbosus, Holotrichia* spp., *Phyllophaga* spp. (such as June beetle (*Phyllophaga crinita*)), and *Diloboderus* spp. (such as *Diloboderus abderus*);

from the family Curculionidae, for example, coffee bean weevil (*Araecerus coffeae*), sweet-potato weevil (*Cylas formicarius*), West Indian sweet-potato weevil (*Euscepes postfasciatus*), alfalfa weevil (*Hypera postica*), maize weevil (*Sitophilus zeamais*), rice plant weevil (*Echinocnemus squameus*), rice water weevil (*Lissorhoptrus oryzophilus*), *Rhabdoscelus lineatocollis*, boll weevil (*Anthonomus grandis*), nunting billbug (*Sphenophorus venatus*), Southern Corn Billbug (*Sphenophorus callosus*), Soybean stalk weevil (*Sternechus subsignatus*), Sugarcane weevil (*Sphenophorus levis*), rusty gourd-shaped weevil (*Scepticus griseus*), brown gourd-shaped weevil (*Scepticus uniformis*), Mexican bean weevil (*Zabrotes subfasciatus*), pine beetle (*Tomicus piniperda*), Coffee Berry Borer (*Hypothenemus hampei*), *Aracanthus* spp. (such as *Aracanthus mourei*), and cotton root borer (*Eutinobothrus brasiliensis*);

from the family Tenebrionidae, for example, red meal beetle (*Tribolium castaneum*) and mason beetle (*Tribolium confusum*);

from the family Coccinellidae, for example, twenty-eight-spotted ladybird (*Epilachna vigintioctopunctata*);

from the family Bostrychidae, for example, common powder-post beetle (*Lyctus brunneus*);

from the family Ptinidae;

from the family Cerambycidae, for example, citrus long-horned beetle (*Anoplophora malasiaca*), and *Migdolus fryanus*;

from the family Elateridae, for example, *Melanotus okinawensis*, barley wireworm (*Agriotes fuscicollis*), *Melanotus legatos*, *Anchastus* spp., *Conoderus* spp., *Ctenicera* spp., *Limonius* spp., and *Aeolus* spp.;

from the family Staphylinidae, for example, *Paederus fuscipes*;

and the others.

Orthoptera:

from the family Acrididae, for example, oriental migratory locust (*Locusta migratoria*), Moroccan locust (*Dociostaurus maroccanus*), Australian plague locust (*Chortoicetes terminifera*), red locust (*Nomadacris septemfasciata*), Brown Locust (*Locustana pardalina*), Tree Locust (*Anacridium melanorhodon*), Italian Locust (*Calliptamus italicus*), Differential grasshopper (*Melanoplus differentialis*), Two striped grasshopper (*Melanoplus bivittatus*), Migratory grasshopper (*Melanoplus sanguinipes*), Red-Legged grasshopper (*Melanoplus femurrubrum*), Clearwinged grasshopper (*Camnula pellucida*), desert locust (*Schistocerca gregaria*), Yellow-winged locust (*Gastrimargus musicus*), Spur-throated locust (*Austracris guttulosa*), Japanese grasshopper (*Oxya yezoensis*), rice grasshopper (*Oxya japonica*), and Bombay locust (*Patanga succincta*);

from the family Gryllotalpidae, for example, oriental mole cricket (*Gryllotalpa orientalis*);

from the family Gryllidae, for example, house cricket (*Acheta domestica*) and emma field cricket (*Teleogryllus emma*);

from the family Tettigoniidae, for example, Mormon cricket (*Anabrus simplex*);

and the others.

Hymenoptera:

from the family Tenthredinidae, for example, beet sawfly (*Athalia rosae*) and nippon cabbage sawfly (*Athalia japonica*);

from the family *Solenopsis* spp.;

from the family Formicidae, for example, Brown leaf-cutting ant (*Atta capiguara*);

and the others.

Blattodea:

from the family Blattellidae, for example, German cockroach (*Blattella germanica*);

from the family Blattidae, for example, smoky-brown cockroach (*Periplaneta fuliginosa*), American cockroach (*Periplaneta americana*), brown cockroach (*Periplaneta brunnea*), and black cockroach (*Blatta orientalis*);

from the family Termitidae, for example, Japanese termite (*Reticulitermes speratus*), Formosan termite (*Coptotermes formosanus*), western drywood termite (*Incisitermes minor*), *Cryptotermes domesticus*, *Odontotermes formosanus*, *Neotermes koshunensis*, *Glyptotermes satsumensis*, *Glyptotermes nakajimai*, *Glyptotermes fuscus*, *Hodotermopsis sjostedti*, *Coptotermes guangzhouensis*, *Reticulitermes amamianus*, *Reticulitermes miyatakei*, *Reticulitermes kanmonensis*, *Nasutitermes takasagoensis*, *Pericapritermes nitobei*, *Sinocapritermes mushae*, and *Cornitermes cumulans*;

and the others.

Acari:

from the family Tetranychidae, for example, common red spider mite (*Tetranychus urticae*), kanzawa spider mite (*Tetranychus kanzawai*), red spider mite (*Tetranychus evansi*), citrus red mite (*Panonychus citri*), fruit-tree red spider mite (*Panonychus ulmi*), and *Oligonychus* spp.;

from the family Eriophyidae, for example, Japanese citrus rust mite (*Aculops pelekassi*), *Phyllocoptruta citri*, tomato mite (*Aculops lycopersici*), purple mite (*Calacarus carinatus*), tea rust mite (*Acaphylla theavagrans*), *Eriophyes chibaensis*, apple bud mite (*Aculus schlechtendali*), *Aceria diospyri*, *Aceria tosichelia*, and *Shevtchenkella* sp.;

from the family Tarsonemidae, for example, broad mite (*Polyphagotarsonemus latus*);

from the family Tenuipalpidae, for example, *Brevipalpus phoenicis*;

from the family Tuckerellidae;

from the family Ixodidae, for example, *Haemaphysalis longicornis*, *Haemaphysalis flava*, *Dermacentor taiwanensis*, American dog tick (*Dermacentor variabilis*), *Ixodes ovatus*, *Ixodes persulcatus*, black-legged tick (*Ixodes scapularis*), lone star tick (*Amblyomma americanum*), cattle tick (*Boophilus microplus*), and brown dog tick (*Rhipicephalus sanguineus*);

from the family Acaridae, for example, cereal mite (*Tyrophagus putrescentiae*) and grassland mite (*Tyrophagus similis*);

from the family Pyroglyphidae, for example, American house dust mite (*Dermatophagoides farinae*) and European house dust mite (*Dermatophagoides pteronyssinus*);

from the family Cheyletidae, for example, *Cheyletus eruditus*, *Cheyletus malaccensis*, *Cheyletus moorei*, and *Cheyletiella yasguri*;

from the family Sarcoptidae, for example, ear mange mite (*Otodectes cynotis*) and itch mite (*Sarcoptes scabiei*);

from the family Demodicidae, for example, dog follicle mite (*Demodex canis*);

from the family Listrophoridae;

from the family Haplochthoniidae;

from the family Macronyssidae, for example, tropical rat mite (*Ornithonyssus bacoti*) and feather mite (*Ornithonyssus sylviarum*);

from the family Dermanyssidae, for example, bird mite (*Dermanyssus gallinae*);

from the family Trombiculidae, for example, *Leptotrombidium akamushi*;

and the others.

Araneae:

from the family Eutichuridae, for example, *Cheiracanthium japonicum*;

from the family Theridiidae, for example, red-back spider (*Latrodectus hasseltii*);

and the others.

Polydesmida:

from the family Paradoxosomatidae, for example, flat-backed millipede (*Oxidus gracilis*) and *Nedyopus tambanus*;

and the others.

Isopoda:

from the family Armadillidiidae, for example, common pill bug (*Armadillidium vulgare*);

and the others.

Chilopoda:
   from the family Scutigeridae, for example, *Thereuonema hilgendorfi*;
   from the family Scolopendridae, for example, giant tropical centipede (*Scolopendra subspinipes*);
   from the family Ethopolidae, for example, *Bothropolys rugosus*;
   and the others.

Gastropoda:
   from the family Limacidae, for example, tree slug (*Limax marginatus*) and garden tawny slug (*Limax flavus*);
   from the family Philomycidae, for example, *Meghimatium bilineatum*;
   from the family Ampullariidae, for example, golden apple snail (*Pomacea canaliculata*);
   from the family Lymnaeidae, for example, *Austropeplea ollula*;
   and the others.

Nematoda:
   from the family Aphelenchoididae, for example, rice white-tip nematode (*Aphelenchoides besseyi*);
   from the family Pratylenchidae, for example, root lesion nematode (*Pratylenchus coffeae*), *Pratylenchus brachyurus*, California meadow nematode (*Pratylenchus neglectus*), and *Radopholus similis*;
   from the family Heteroderidae, for example, javanese root-knot nematode (*Meloidogyne javanica*), southern root-knot nematode (*Meloidogyne incognita*), northern root-knot nematode (*Meloidogyne hapla*), soybean cyst nematode (*Heterodera glycines*), potato cyst nematode (*Globodera rostochiensis*), and white potato cyst nematode (*Globodera pallida*);
   from the family Hoplolaimidae, for example, *Rotylenchulus reniformis*;
   from the family Anguinidae, for example, strawberry bud nematode (*Nothotylenchus acris*) and stem nematode (*Ditylenchus dipsaci*);
   from the family Tylenchulidae, for example, citrus nematode (*Tylenchulus semipenetrans*);
   from the family Longidoridae, for example, dagger nematode (*Xiphinema index*);
   from the family Trichodoridae;
   from the family Parasitaphelenchidae, for example, pine wilt disease (*Bursaphelenchus xylophilus*);
   and the others.

The target harmful insects and harmful mites may have a reduced agent-sensitivity to or a developed agent-resistance to an insecticide or a miticide. However, when the agent-sensitivity is greatly reduced or the agent-resistance is greatly developed, a composition of the present invention comprising an insecticide and a miticide other than the intended insecticide and miticide is preferably used.

The compound of the present invention may be also used to protect a plant from a plant disease caused by insect-borne viruses or insect-borne bacteria.

Examples of the insect-borne viruses are recited as follows.

Rice tungro spherical virus, Rice tungro bacilliform virus, Rice grassy stunt virus, Rice ragged stunt virus, Rice stripe virus, Rice black streaked dwarf virus, Southern rice black-streaked dwarf virus, Rice gall dwarf virus, Rice hoja blanca virus, Rice yellow stunt virus, Rice yellow mottle virus, Rice dwarf virus, Northern cereal mosaic virus, Barley yellow dwarf virus, Barley mild mosaic virus, Barley yellow dwarf virus-PAV, Cereal yellow dwarf virus-RPS, Wheat yellow leaf virus, Oat sterile dwarf virus, Wheat streak mosaic virus, Maize dwarf mosaic virus, Maize stripe virus, Maize chlorotic mottle virus, Maize chlorotic dwarf virus, Maize rayado fino virus, Sugarcane mosaic virus, Fiji disease virus, Sugarcane yellow leaf virus, Soybean mild mosaic virus, Cycas necrotic stunt, Soybean dwarf virus, Milk vetch dwarf virus, Soybean mosaic virus, Alfalfa mosaic virus, Bean yellow mosaic virus, Bean common mosaic virus, Southern bean mosaic virus, Peanut stunt virus, Broad bean wilt virus 1, Broad bean wilt virus 2, Broad bean necrosis virus, Broad bean yellow vein virus, Clover yellow vein virus, Peanut mottle virus, Tobacco streak virus, Bean pod mottle virus, Cowpea chlorotic mottle virus, Mung bean yellow mosaic virus, Soybean crinkle leaf virus, Tomato chlorosis virus, Tomato spotted wilt virus, Tomato yellow leaf curl virus, Tomato aspermy virus, Tomato infectious chlorosis virus, Potato leafroll virus, Potato virus Y, Melon yellow spot virus, Melon necrotic spot virus, Watermelon mosaic virus, Cucumber mosaic virus, Zucchini yellow mosaic virus, Turnip mosaic virus, Turnip yellow mosaic virus, Cauliflower mosaic virus, Lettuce mosaic virus, Celery mosaic virus, Beet mosaic virus, Cucurbit chlorotic yellows virus, Capsicum chlorosis virus, Beet pseudo yellows virus, Leak yellow stripe virus, Onion yellow dwarf virus, Sweet potato feathery mottle virus, Sweet potato shukuyo mosaic virus, Strawberry mottle virus, Strawberry mild yellow edge virus, Strawberry pseudo mild yellow edge virus, Strawberry crinkle virus, Strawberry vein banding virus, plum pox virus, Chrysanthemum stem necrosis virus, Impatiens necrotic spot virus, Iris yellow spot virus, Lily mottle cirus, Lilly symptomless virus, Tulip mosaic virus, and the others.

Examples of the insect-borne bacteria are recited as follows.

Candidatus Phytoplasma oryzae, Candidatus Phytoplasma asteris, Maize bushy stunt phytoplasma, Candidatus Liberbacter asiaticus, Candidatus Liberbacter africanus, Candidatus Liberbacter americanus, and the others.

The composition for controlling harmful arthropods of the present invention (hereinafter, which may be referred to as "Composition of the present invention") comprises the compound of the present invention and an inert carrier. The composition for controlling harmful arthropods of the present invention is usually prepared by mixing the compound of the present invention with an inert carrier such as solid carrier, liquid carrier and gaseous carrier, and if necessary, adding surfactants and the other auxiliary agents for formulation, to formulate into emulsifiable concentrates, oil solutions, powders, granules, wettable powders, water dispersible granules, flowables, dry flowables, microcapsules, aerosols, poison baits, resin formulations, shampoo formulations, paste formulations, foams, carbon dioxide formulations, tablets and the others. Such formulations may be processed into mosquito repellent incenses, electric mosquito repellent mats, mosquito repellent liquid formulations, smoking formulations, fumigants, sheet formulations, spot-on formulations or formulations for oral treatment. The composition for controlling harmful arthropods of the present invention comprises usually 0.01 to 95% by weight of the compound of the present invention.

Examples of the solid carrier used in the formulation include fine powders or granules such as clays (for example, kaolin clay, diatomaceous earth, bentonite, Fubasami clay, and acid white clay), dry silica, wet silica, talcs, ceramics, other inorganic minerals (for example, sericite, quartz, sulfur, active carbon, and calcium carbonate), and chemical fertilizers (for example, ammonium sulfate, ammonium phosphate, ammonium nitrate, urea, and ammonium chloride) and the others, as well as synthetic resins (for example, polyester resins such as polypropylene, polyacrylonitrile, polymethyl methacrylate and polyethylene terephthalate; nylon resins such as nylon-6, nylon-11 and nylon-66; polyamide resins; polyvinyl chloride, polyvinylidene chloride, vinyl chloride-propylene copolymers, and the others).

Examples of the liquid carriers include water; alcohols (for example, methanol, ethanol, isopropyl alcohol, butanol, hexanol, benzyl alcohol, ethylene glycol, propylene glycol and phenoxy ethanol); ketones (for example, acetone, methyl ethyl ketone and cyclohexanone); aromatic hydrocarbons (for example, toluene, xylene, ethylbenzene, dodecylbenzene, phenylxylylethane and methylnaphthalene); aliphatic hydrocarbons (for example, hexane, cyclohexane, kerosene and light oil); esters (for example, ethyl acetate, butyl acetate, isopropyl myristate, ethyl oleate, diisopropyl adipate, diisobutyl adipate and propylene glycol monomethyl ether acetate); nitriles (for example, acetonitrile and isobutyronitrile); ethers (for example, diisopropyl ether, 1,4-dioxane, 1,2-dimethoxyethane, diethyleneglycol dimethyl ether, diethylene glycol monomethyl ether, propylene glycol monomethyl ether, dipropylene glycol monomethyl ether and 3-methoxy-3-methyl-1-butanol); amides (for example, DMF and N,N-dimethylacetamide); sulfoxides (for example, dimethyl sulfoxide); propylene carbonate; and vegetable oils (for example, soybean oil and cottonseed oil).

Examples of the gaseous carrier include fluorocarbon, butane gas, LPG (liquefied petroleum gas), dimethyl ether, and carbon dioxide gas.

Examples of the surfactants include nonionic surfactants such as polyoxyethylene alkyl ethers, polyoxyethylene alkyl aryl ethers and polyethylene glycol fatty acid esters; and anionic surfactants such as alkyl sulfonates, alkylbenzene sulfonates and alkyl sulfates.

Examples of the other auxiliary agents for formulation include, a binder, a dispersant, a colorant and a stabilizer, and specific examples thereof include casein, gelatin, saccharides (for example, starch, gum arabic, cellulose derivatives and alginic acid), lignin derivatives, bentonite, water-soluble synthetic polymers (for example, polyvinyl alcohol, polyvinyl pyrrolidone and polyacrylic acids); acidic isopropyl phosphate, 2,6-di-tert-butyl-4-methylphenol, and BHA (a mixture of 2-tert-butyl-4-methoxyphenol and 3-tert-butyl-4-methoxyphenol).

Examples of a base material for the resin formulation include polyvinyl chloride polymers and polyurethane, and if necessary, a plasticizer such as phthalate esters (for example, dimethyl phthalate and dioctyl phthalate), adipic acid esters and stearic acid may be added to these base materials. The resin formulation can be prepared by mixing the compound with the above base material using a typical kneading machine, followed by molding the mixture by injection molding, extrusion molding, pressure molding and the like, and may be processed into the resin formulation having shapes such as a plate, a film, a tape, a net and a string through further steps such as molding and cutting as needed. These resin formulations can be processed into, for example, animal collars, animal ear tags, sheet products, attractant strings, gardening supports.

Examples of a base material for the poison baits include grain powder, vegetable oil, saccharide and crystalline cellulose, and if necessary, may be subject to further addition of antioxidants (for example, dibutylhydroxytoluene and nordihydroguaiaretic acid), preservatives (for example, dehydroacetic acid), accidental ingestion inhibitors for children and pets (for example, a chili powder), pest attraction fragrances (for example, cheese fragrance, onion fragrance and peanut oil), and the others.

The method for controlling harmful arthropods of the present invention is carried out by applying an effective amount of the compound of the present invention to harmful arthropods directly and/or a habitat of pests (for example, plants, soils, indoor areas, animal bodies). Also, the method for controlling harmful arthropods of the present invention may be applied to seeds. In the method for controlling harmful arthropods of the present invention, the compound of the present invention is usually used in the form of a composition for controlling harmful arthropods of the present invention.

When the composition for controlling harmful arthropods of the present invention is used for controlling harmful arthropods in an agricultural field, an application dose as an amount of the compound of the present invention is usually within a range of 1 to 10,000 g per 10,000 m$^2$. In the case of being applied to seeds, the application dose as an amount of the compound of the present invention is usually within a range of 0.001 to 100 g per 1 kg of the seeds. When the composition for controlling harmful arthropods of the present invention is formulated into emulsifiable concentrates, wettable powders, flowables and the like, the composition of the present invention is usually applied by diluting it with water in such a way that a concentration of the active ingredient is within a range of 0.01 to 10,000 ppm. The granular formulation, or the dust formulation etc., is usually applied as itself without diluting it.

These formulations or an aqueous dilution thereof can be sprayed directly to harmful arthropods or plants such as crops to be protected from harmful arthropods, and also may be applied to the soil of crop land in order to control pests which live there.

Also, the resin preparation which is processed into a sheet or a string may be applied by winding a plant with a sheet or a string of the resin preparation, putting a string of the resin preparation around a crop so that the plant is surrounded by the string, or laying a sheet of the resin preparation on the soil surface near the root of a plant.

When the composition for controlling harmful arthropods of the present invention is used to control pests that live inside a house, in the case of using it on a planar area, an application dose of the compound of the present invention is usually within a range of 0.01 to 1,000 mg per 1 m$^2$ of the area to be treated, while in the case of using it spatially, an application dose of the compound of the present invention is usually within a range of 0.01 to 500 mg per 1 m$^3$ of the space to be treated. When the composition for controlling harmful arthropods of the present invention is formulated into emulsifiable concentrates, wettable powders, flowables and the like, these formulations are usually applied after diluting it with water in such a way that a concentration of the active ingredient is within a range of 0.1 to 10,000 ppm, and then sparging it. In the case of being formulated into oil solutions, aerosols, smoking formulations, poison baits and the like, such formulations are used as itself without diluting it.

When the composition for controlling harmful arthropods of the present invention is used in order to control external parasites of livestock (for example, cows, horses, pigs, sheep, goats and chickens) and small animals (for example, dogs, cats, rats and mice), the composition can be applied to the animals by a known method in the veterinary field. For specific methods of use, when systemic control is intended, the composition is administered to the animals as a tablet, a mixture with feed, a suppository, or by injections (for example, intramuscular injections, subcutaneous injections, intravenous injections and intraperitoneal injections). When non-systemic control is intended, the composition is applied to the animals by means of spraying of the oil solution or aqueous solution, conducting pour-on or spot-on treatments, washing of the animal with the shampoo formulation, or by putting the collar or ear tag made of the resin formulations to the animal. In the case of being administered to an animal body, an application dose of the compound of the present invention is usually within a range of 0.1 to 1,000 mg per 1 kg of the animal body weight.

Also, the compound of the present invention can be used as an agent for controlling harmful arthropods in agricultural land such as fields, paddy fields, turfs, and orchards. The compound of the present invention can control harmful arthropods in agricultural land where plants and the others as described below are cultivated.

Crops: corn, rice, wheat, barley, rye, oat, sorghum, cotton, soybean, peanut, buckwheat, beet, rapeseed, sunflower, sugar cane, tobacco, and the others;

Vegetables: solanaceous vegetables (eggplant, tomato, pimento, capsicum, potato, etc.), cucurbitaceous vegetables (cucumber, pumpkin, zucchini, water melon, melon, etc.), cruciferous vegetables (Japanese radish, white turnip, horseradish, kohlrabi, Chinese cabbage, cabbage, leaf mustard, broccoli, cauliflower, etc.), asteraceous vegetables (burdock, crown daisy, artichoke, lettuce, etc.), liliaceous vegetables (welsh onion, onion, garlic, asparagus), apiaceous vegetables (carrot, parsley, celery, parsnip, etc.), chenopothaceous vegetables (spinach, Swiss chard, etc.), lamiaceous vegetables (*Perilla frutescens*, mint, basil, etc.), strawberry, sweet potato, glutinous yam, eddoe, and the others; flowers; foliage plants;

Fruits: pomaceous fruits (apple, pear, Japanese pear, Chinese quince, quince, etc.), stone fleshy fruits (peach, plum, nectarine, Japanese plum, cherry fruit, apricot, prune, etc.), citrus fruits (Citrus unshiu, orange, lemon, lime, grapefruit, etc.), nuts (chestnuts, walnuts, hazelnuts, almond, pistachio, cashew nuts, macadamia nuts, etc.), berries (blueberry, cranberry, blackberry, raspberry, etc.), grapes, Japanese persimmon, olive, loquat, banana, coffee, date palm, coconuts, and the others;

Trees other than fruit trees: tea, mulberry, flowering trees, roadside trees (ash, birch, dogwood, eucalyptus, *Ginkgo biloba*, lilac, maple, oak, poplar, cercis, Liquidambar formosana, plane tree, zelkova, Japanese arborvitae, fir tree, hemlock, juniper, pine, spruce, and yew), and the others.

The plants described above also include genetically modified crops.

EXAMPLES

Hereinafter, the present invention is described in more detail by the following examples including Preparation Examples, Formulation Examples, and Test Examples, however, the present invention should not be limited thereto.

First, Preparation Examples of the compounds are shown.

Preparation Example 1

A mixture of 21.0 g of 3-amino-1,2,4-triazole, 60.0 g of di-tert-butyl dicarbonate, 1.45 g of tetramethylethylenediamine and 500 mL of hexane was stirred at room temperature for 12 hours. Water was added to the resulting mixture, and the mixture was extracted with ethyl acetate. The resulting organic layer was washed with saturated brine, dried over anhydrous magnesium sulfate, and concentrated under reduced pressure. The resulting residue was subjected to silica gel chromatography to obtain 15.6 g of intermediate compound (1) and 1.06 g of the intermediate compound (2), both of which being represented by the following formulae.

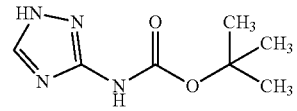

Intermediate compound (1): $^{1}$H-NMR (CDCl$_3$) δ: 7.47 (1H, s), 6.21 (1H, br s), 1.65 (9H, s).

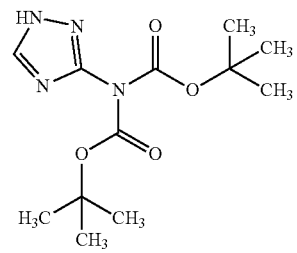 [SMILES: CC(C)(C)OC(=O)N(C(=O)OC(C)(C)C)c1nc[nH]n1]

Intermediate compound (2): $^{1}$H-NMR (CDCl$_3$) δ: 8.56 (1H, s), 1.65 (18H, s).

Preparation Example 2

A mixture of 20.02 g of 3-amino-1,2,4-triazole, 35.27 g of 4-methoxybenzaldehyde, 30.11 g of DMF and 30.09 g of toluene was stirred under reflux for 5.5 hours. During the reaction, water was removed using a Dean-Stark apparatus. The resulting mixture was cooled to room temperature, and then the precipitated solid was filtered. The resulting solid was dried under reduced pressure to obtain 46.01 g of the intermediate compound (3) represented by the following formula.

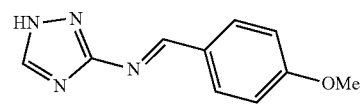 [SMILES: COc1ccc(/C=N/c2nc[nH]n2)cc1]

Intermediate compound (3): $^{1}$H-NMR (CDCl$_3$) δ: 11.17-10.90 (1H, m), 9.25 (1H, s), 8.00-7.90 (3H, m), 7.00 (2H, d, J=8.9 Hz), 3.89 (3H, s).

Preparation Example 3

A mixture of 2.00 g of 3-amino-1,2,4-triazole, 4.00 g of toluene, and 4.21 g of N,N-dimethylformamide dimethyl acetal was stirred at 50° C. for 5 hours. After the resulting mixture was cooled to room temperature, the precipitated solid was filtered, and the resulting solid was dried under reduced pressure to obtain 2.56 g of the intermediate compound (4) represented by the following formula.

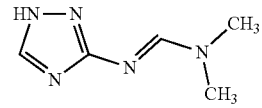

Intermediate compound (4): $^1$H-NMR (DMSO-d$_6$) δ: 12.83 (1H, s), 8.38 (1H, s), 7.57 (1H, s), 3.09 (3H, s), 2.93 (3H, s).

Preparation Example 4

To a mixture of 8.00 g of 3-amino-1,2,4-triazole and 32.65 g of DMF was added 10.09 g of methyl chloroformate at room temperature, and the mixture was stirred at 40° C. for 2 hours. The resulting mixture was cooled to room temperature, water was added thereto, and the precipitated solid was collected by filtration to obtain 5.67 g of the intermediate compound (5) represented by the following formula.

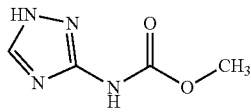

Intermediate compound (5): $^1$H-NMR (DMSO-d$_6$) δ: 7.56 (1H, s), 7.36 (1H, s), 3.93 (3H, s).

Preparation Example 5

A mixture of 8.10 g of 2-[6-chloro-3-(ethanesulfonyl)pyridin-2-yl]-3-methyl-6-(trifluoromethyl)-3H-imidazo[4,5-b]pyridine (hereinafter referred to as Intermediate compound (8)), 2.52 g of 3-amino-1,2,4-triazole, 13.0 g of cesium carbonate and 80 mL of DMF was stirred at 0° C. for 8 hours. Water was added to the resulting mixture, and the mixture was extracted with chloroform. The resulting organic layer was washed with saturated brine, dried over anhydrous sodium sulfate, and concentrated under reduced pressure. The resulting residue was subjected to silica gel chromatography to obtain 4.38 g of the intermediate compound (9) represented by the following formula.

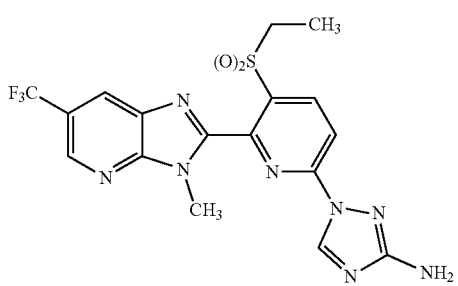

Intermediate compound (9): $^1$H-NMR (DMSO-d$_6$) δ: 9.08 (1H, s), 8.89 (1H, d, J=1.4 Hz), 8.68 (1H, d, J=1.4 Hz), 8.62 (1H, d, J=8.6 Hz), 7.94 (1H, d, J=8.6 Hz), 6.17 (2H, br s), 3.85-3.83 (5H, m), 1.21 (3H, t, J=7.5 Hz).

Preparation Example 6

A mixture of 0.50 g of the intermediate compound (8), 0.28 g of the intermediate compound (1), 0.34 g of potassium carbonate and 2.00 g of DMF was stirred at 70° C. for 16 hours. The resulting mixture was cooled to room temperature, water was added thereto, and the mixture was extracted with ethyl acetate. The resulting organic layer was washed with saturated brine, dried over anhydrous sodium sulfate, and concentrated under reduced pressure. The resulting residue was subjected to silica gel chromatography to obtain 0.49 g of the compound A3 represented by the following formula.

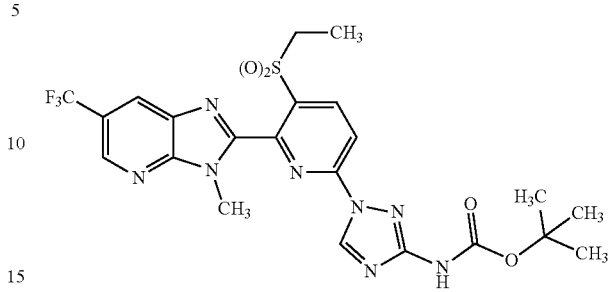

Compound A3: $^1$H-NMR (CDCl$_3$) δ: 8.95 (1H, s), 8.80 (1H, d, J=1.4 Hz), 8.65 (1H, d, J=8.7 Hz), 8.34 (1H, d, J=1.4 Hz), 8.28 (1H, d, J=8.7 Hz), 7.54 (1H, s), 3.90 (3H, s), 3.78 (2H, q, J=7.4 Hz), 1.57 (9H, s), 1.38 (3H, t, J=7.4 Hz).

Preparation Example 7

The compounds which were prepared according to the method described in Preparation Example 6 and physical property values thereof are shown below.

The compound represented by formula (I-B):

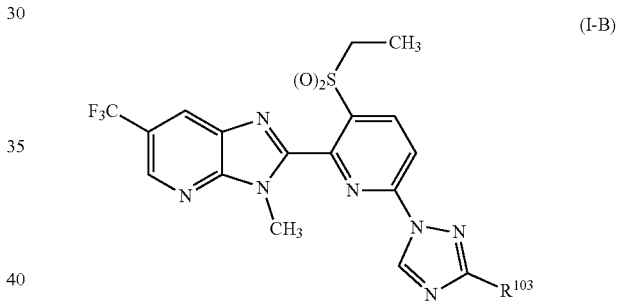

wherein $R^{103}$ is any one of those listed in Table 5.

TABLE 5

| Compound | $R^{103}$ |
|---|---|
| A2 | NBoc$_2$ |
| A4 | NHC(O)OMe |
| A8 | —N=CH-N(CH$_3$)$_2$ |
| A9 | —N=CH-C$_6$H$_4$-OMe |

Compound A2: $^1$H-NMR (CDCl$_3$) δ: 9.10 (1H, s), 8.81 (1H, d, J=1.4 Hz), 8.71 (1H, d, J=8.6 Hz), 8.35 (1H, d, J=1.6 Hz), 8.25 (1H, d, J=8.6 Hz), 3.93 (3H, s), 3.81 (2H, q, J=7.5 Hz), 1.50 (18H, s), 1.39 (3H, t, J=7.4 Hz).

Compound A4: $^1$H-NMR (CDCl$_3$) δ: 8.98 (1H, s), 8.81 (1H, s), 8.68 (1H, d, J=8.6 Hz), 8.35 (1H, s), 8.28 (1H, d, J=8.6 Hz), 8.21-8.13 (1H, m), 3.91 (3H, s), 3.88 (3H, s), 3.78 (2H, q, J=7.3 Hz), 1.38 (3H, t, J=7.3 Hz).

Compound A8: $^1$H-NMR (CDCl$_3$) δ: 8.91 (1H, s), 8.79 (1H, d, J=1.6 Hz), 8.62 (1H, d, J=8.8 Hz), 8.55 (1H, s), 8.33 (1H, d, J=1.6 Hz), 8.23 (1H, d, J=8.8 Hz), 3.91 (3H, s), 3.76 (2H, q, J=7.4 Hz), 3.16 (3H, s), 3.14 (3H, s), 1.37 (3H, t, J=7.4 Hz).

Compound A9: $^1$H-NMR (CDCl$_3$) δ: 9.32 (1H, s), 9.10 (1H, s), 8.82-8.79 (1H, m), 8.71 (1H, d, J=8.6 Hz), 8.36-8.34 (2H, m), 8.03 (2H, d, J=8.8 Hz), 7.02 (2H, d, J=8.8 Hz), 3.94 (3H, s), 3.90 (3H, s), 3.80 (2H, q, J=7.4 Hz), 1.39 (3H, t, J=7.4 Hz).

Preparation Example 8

To a mixture of 0.45 g of the intermediate compound (9), 0.24 g of pyridine and 4 mL of chloroform was added 0.11 g of ethyl chloroformate, and the mixture was stirred at room temperature for 4 hours. Water was added to the resulting mixture, and the mixture was extracted with chloroform. The resulting organic layer was washed with saturated brine, dried over anhydrous magnesium sulfate, and concentrated under reduced pressure. The resulting residue was subjected to silica gel chromatography to obtain 0.15 g of the compound A$^1$ represented by the following formula.

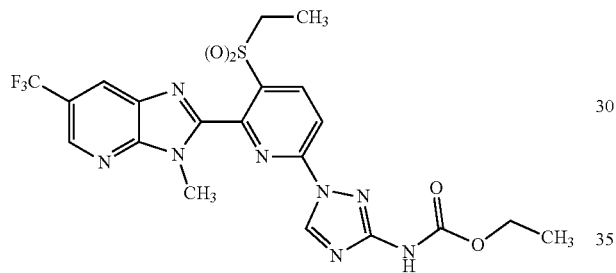

Compound A1: $^1$H-NMR (CDCl$_3$) δ: 8.97 (1H, s), 8.80 (1H, d, J=1.6 Hz), 8.67 (1H, d, J=8.7 Hz), 8.35 (1H, d, J=1.6 Hz), 8.28 (1H, d, J=8.7 Hz), 8.09 (1H, s), 4.33 (2H, q, J=7.1 Hz), 3.91 (3H, s), 3.78 (2H, q, J=7.5 Hz), 1.41-1.33 (6H, m).

Preparation Example 9

The compounds which were prepared according to the method described in Preparation Example 8 and physical property values thereof are shown below.

The compound represented by formula (I-A):

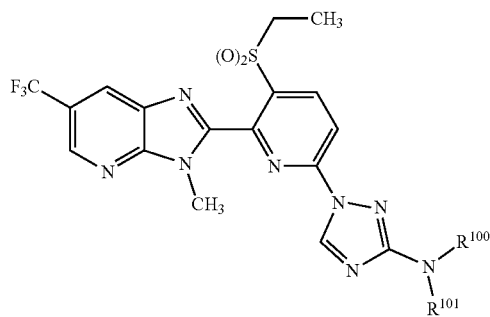

wherein a combination of R$^{100}$ and R$^{101}$ is any one of those listed in Table 6.

TABLE 6

| Compound | R$^{100}$ | R$^{101}$ |
|---|---|---|
| A4 | C(O)OMe | H |
| A6 | C(O)OPr | H |

Compound A6: $^1$H-NMR (CDCl$_3$) δ: 8.97 (1H, s), 8.80 (1H, s), 8.66 (1H, d, J=8.7 Hz), 8.35 (1H, s), 8.27 (1H, d, J=8.7 Hz), 4.22 (2H, t, J=6.6 Hz), 3.90 (3H, s), 3.78 (2H, q, J=7.4 Hz), 1.79-1.69 (2H, m), 1.37 (3H, t, J=7.4 Hz), 0.98 (3H, t, J=7.4 Hz).

Preparation Example 10

To a mixture of 0.45 g of the intermediate compound (9), 0.24 g of pyridine and 4 mL of chloroform was added 0.18 g of ethyl chloroformate, and the mixture was stirred at room temperature for 2 hours. Water was added to the resulting mixture, and the mixture was extracted with chloroform. The resulting organic layer was washed with saturated brine, dried over anhydrous magnesium sulfate, and concentrated under reduced pressure. The resulting residue was subjected to silica gel chromatography to obtain 0.030 g of the compound A7 represented by the following formula.

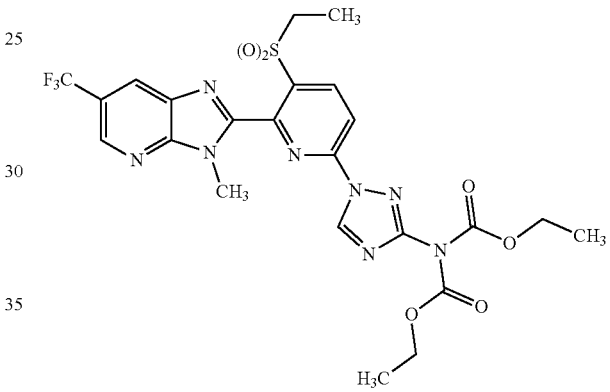

Compound A7: $^1$H-NMR (CDCl$_3$) δ: 9.13 (1H, s), 8.80 (1H, s), 8.72 (1H, d, J=8.6 Hz), 8.35 (1H, s), 8.24 (1H, d, J=8.6 Hz), 4.31 (4H, q, J=7.0 Hz), 3.94 (3H, s), 3.81 (2H, q, J=7.5 Hz), 1.38 (3H, t, J=7.5 Hz), 1.28 (6H, t, J=7.0 Hz).

Preparation Example 11

The compound A5 which was prepared according to the method described in Preparation Example 10 and physical property value thereof is shown below.

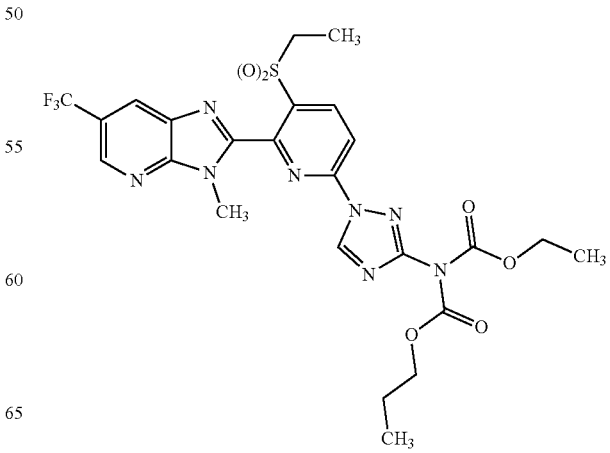

compound A5: ¹H-NMR (CDCl₃) δ: 9.14 (1H, s), 8.81 (1H, d, J=1.4 Hz), 8.73 (1H, d, J=8.5 Hz), 8.36 (1H, d, J=1.4 Hz), 8.24 (1H, d, J=8.5 Hz), 4.23 (4H, t, J=6.6 Hz), 3.95 (3H, s), 3.82 (2H, q, J=7.4 Hz), 1.73-1.63 (4H, m), 1.39 (3H, t, J=7.4 Hz), 0.91 (6H, t, J=7.4 Hz).

Preparation Example 12

A mixture of 0.45 g of the intermediate compound (9) and 5 mL of N,N-dimethylformamide dimethyl acetal was stirred at 90° C. for 2 hours. Water was added to the mixture, and the mixture was extracted with chloroform. The resulting organic layer was washed with saturated brine, dried over anhydrous magnesium sulfate, and concentrated under reduced pressure to obtain 0.30 g of the compound A8 represented by the following formula.

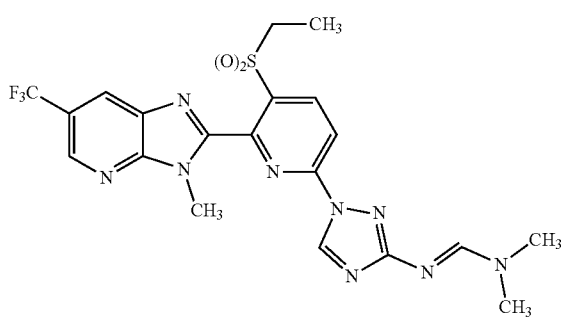

Preparation Example 13

A mixture of 0.42 g of 6-chloro-3-(ethylsulfonyl)-N-[2-(methylamino)-5-(trifluoromethyl)pyridin-3-yl]pyridine-2-carboxamide, 0.20 g of the intermediate compound (3), 0.28 g of potassium carbonate and 4 mL of THF was stirred at 60° C. for 4 hours. Water was added to the resulting mixture, and the mixture was extracted with ethyl acetate. The resulting organic layer was washed with saturated brine, dried over anhydrous magnesium sulfate, and concentrated under reduced pressure. The resulting residue was subjected to silica gel chromatography to obtain 0.28 g of the compound C1 represented by the following formula.

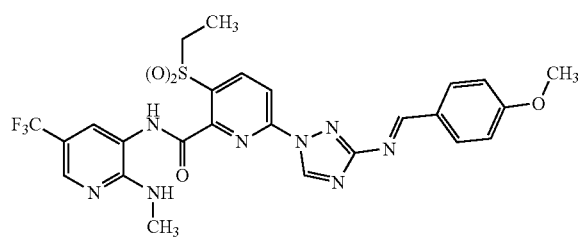

Compound C1: ¹H-NMR (CDCl₃) δ: 9.29 (1H, s), 9.16 (1H, s), 8.51 (1H, d, J=8.6 Hz), 8.41 (1H, d, J=0.9 Hz), 8.22 (1H, d, J=8.6 Hz), 8.14 (1H, d, J=0.9 Hz), 8.01 (2H, d, J 8.8 Hz), 7.75-7.73 (1H, m), 7.02 (2H, d, J=8.8 Hz), 5.93-5.87 (1H, m), 3.91 (3H, s), 3.73 (2H, q, J=7.5 Hz), 3.04 (3H, d, J=4.5 Hz), 1.37 (3H, t, J=7.5 Hz).

Preparation Example 14

The compounds which were prepared according to the method described in Preparation Example 13 and physical property values thereof are shown below.

The compound represented by formula (I-C):

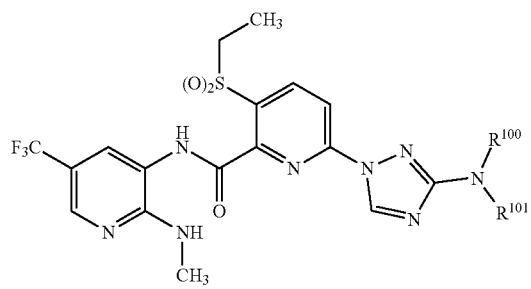

(I-C)

wherein a combination of R¹⁰⁰ and R¹⁰¹ is any one of those listed in Table 7.

TABLE 7

| Compound | R¹⁰⁰ | R¹⁰¹ |
| --- | --- | --- |
| C2 | H | C(O)Ot-Bu |
| C3 | H | C(O)OMe |

Compound C2: ¹H-NMR (DMSO-d₆) δ: 10.43 (1H, s), 10.32 (1H, s), 9.62 (1H, s), 8.66 (1H, d, J=8.8 Hz), 8.37 (1H, d, J=1.1 Hz), 8.06 (1H, d, J=8.4 Hz), 7.92 (1H, dd, J=5.7, 3.5 Hz), 6.65 (1H, d, J=4.8 Hz), 3.70 (2H, q, J=7.4 Hz), 2.95 (3H, d, J=4.4 Hz), 1.49 (9H, s), 1.22 (3H, t, J=7.5 Hz).

Compound C3: ¹H-NMR (DMSO-d₆) δ: 10.67 (1H, s), 10.43 (1H, s), 9.65 (1H, s), 8.67 (1H, d, J=8.8 Hz), 8.38-8.36 (1H, m), 8.06 (1H, d, J=8.4 Hz), 7.91 (1H, d, J=2.2 Hz), 6.66-6.62 (1H, m), 3.74-3.67 (5H, m), 2.95 (3H, d, J=4.8 Hz), 1.22 (3H, t, J=7.5 Hz).

Preparation Example 15

A mixture of 0.20 g of compound C3, 1.01 g of propylene glycol and 0.17 g of lactic acid was stirred at 135° C. for 14 hours. The resulting reaction mixture was added to 20.06 g of water, and the precipitated solid was collected by filtration, dried under reduced pressure, and then analyzed by high performance liquid chromatography to confirm that the compound A4 was obtained.

Next, Formulation Examples of the compounds are shown below. Herein, "part" represents "part by weight".

Formulation Example 1

Ten (10) parts of any one of the compounds A1 to A9 are mixed with a mixture of 35 parts of xylene and 35 parts of DMF, and then 14 parts of polyoxyethylene styryl phenyl ether and 6 parts of calcium dodecylbenzenesulfonate are added thereto and mixed to obtain a formulation.

Formulation Example 2

Four (4) parts of sodium lauryl sulfate, 2 parts of calcium lignin sulfonate, 20 parts of wet silica and 54 parts of diatomaceous earth are mixed, and then 20 parts of any one of the compounds A1 to A9 is added thereto and mixed to obtain a formulation.

Formulation Example 3

To 2 parts of any one of the compounds A1 to A9 are added 1 part of wet silica, 2 parts of calcium lignin sulfonate, 30 parts of bentonite and 65 parts of kaolin clay, and the mixture is mixed. Then, an appropriate amount of water is added to the mixture, and the mixture is further stirred, granulated with a granulator, and forced-air dried to obtain a formulation.

Formulation Example 4

One (1) part of any one of the compounds A1 to A9 is mixed with an appropriate amount of acetone, and 5 parts of wet silica, 0.3 parts of isopropyl acid phosphate and 93.7 parts of kaolin clay are added thereto, followed by mixing with stirring thoroughly, and removal of acetone from the mixtures by evaporation to obtain a formulation.

Formulation Example 5

Thirty-five (35) parts of a mixture of polyoxyethylene alkyl ether sulfate ammonium salt and wet silica (weight ratio 1:1), 20 parts of any one of the compounds A1 to A9, and 45 parts of water are mixed thoroughly to obtain a formulation.

Formulation Example 6

Into a mixture of 5 parts of xylene and 5 parts of trichloroethane, 0.1 parts of any one of the compounds A1 to A9 is added, followed by mixing, and the resulting mixture is then mixed with 89.9 parts of kerosene to obtain formulation.

Formulation Example 7

Ten (10) mg of any one of the compounds A1 to A9 are mixed with 0.5 mL of acetone, and the solution is added dropwise to 5 g of solid feed powder for animals (solid feed powder for rearing and breeding CE-2, manufactured by CLEA Japan, Inc.), followed by mixing the resulting mixture uniformly and then by drying them by evaporation of acetone to obtain poison baits.

Formulation Example 8

Into an aerosol can, 0.1 parts of any one of the compounds A1 to A9 and 49.9 parts of Neothiozole (manufactured by Chuo Kasei Co., Ltd.) are placed, and after mounting an aerosol valve, 25 parts of dimethyl ether and 25 parts of LPG are filled and shaken, followed by mounting an actuator to obtain an oily aerosol.

Formulation Example 9

A mixture of 0.6 parts of any one of the compounds A1 to A9, 0.01 part of 2,6-di-tert-butyl-4-methylphenol, 5 parts of xylene, 3.39 parts of kerosene and 1 part of an emulsifier {Rheodol MO-60 (manufactured by Kao Corporation)}, and 50 parts of distilled water are filled into an aerosol container, and a valve part is attached, and 40 parts of propellant (LPG) is filled under pressure through the valve to obtain an aqueous aerosol.

Formulation Example 10

Zero point one (0.1) g of any one of the compounds A1 to A9 is mixed with 2 mL of propylene glycol, and the mixture is impregnated into a ceramic plate having a size of 4.0 cm×4.0 cm and a thickness of 1.2 cm to obtain a thermal fumigant.

Formulation Example 11

Five (5) parts of any one of the compounds A1 to A9 and 95 parts of ethylene-methyl methacrylate copolymer (a ratio by weight of methyl methacrylate to the total amount of the copolymer: 10% by weight, Acryft (registered trademark) WD301, manufactured by Sumitomo Chemical Co. Ltd.) are melted and kneaded with a closed type pressure kneader (manufactured by Moriyama Manufacturing Co. Ltd.), and the resulting kneaded product is extruded from an extrusion molding machine through a molding dice to obtain a rod-shaped molded product having a length of 15 cm and a diameter of 3 mm.

Formulation Example 12

Five (5) parts of any one of the compounds A1 to A9 and 95 parts of plasticized vinyl chloride resin are melted and kneaded with a closed type pressure kneader (manufactured by Moriyama Manufacturing Co. Ltd.), and the resulting kneaded product is extruded from an extrusion molding machine through a molding dice to obtain a rod-shaped molded product having a length of 15 cm and a diameter of 3 mm.

Formulation Example 13

One hundred (100) mg of any one of the compounds A1 to A9, 68.75 mg of lactose, 237.5 mg of corn starch, 43.75 mg of microcrystalline cellulose, 18.75 mg of polyvinylpyrrolidone, 28.75 mg of sodium carboxymethyl starch, and 2.5 mg of magnesium stearate are mixed, and the resulting mixture is compressed to an appropriate size to obtain a tablet.

Formulation Example 14

Twenty five (25) mg of any one of the compounds A1 to A9, 60 mg of lactose, 25 mg of corn starch, 6 mg of carmellose calcium, and an appropriate amount of 5% hydroxypropylmethyl cellulose are mixed, and the resulting mixture is filled into a hard shell gelatin capsule or hydroxypropylmethyl cellulose capsule to obtain a capsule.

Formulation Example 15

To 100 mg of any one of the compounds A1 to A9, 500 mg of fumaric acid, 2,000 mg of sodium chloride, 150 mg of methylparaben, 50 mg of propylparaben, 25,000 mg of granulated sugar, 13,000 mg of sorbitol (70% solution), 100 mg of Veegum (registered trademark) K (Vanderbilt Co.), 35 mg of a fragrance and 500 mg of a colorant, a distilled water is added so as to have 100 ml as a final volume, followed by mixing them to obtain a suspension for oral administration.

Formulation Example 16

Five (5) % by weight of any one of the compounds A1 to A9 is mixed with 5% by weight of an emulsifier, 3% by weight of benzyl alcohol, and 30% by weight of propylene glycol, and a phosphate buffer is added thereto so as to make the pH of the solution 6.0 to 6.5, and then water is added as the rest parts to obtain a solution formulation for oral administration.

Formulation Example 17

Five (5) % by weight of aluminum distearate is added to 57% by weight of fractional distilled palm oil and 3% by weight of polysorbate 85, and the mixture is heated to disperse. The resulting mixture is cooled to room temperature, and 25% by weight of saccharin is dispersed in the oily vehicle. Ten (10) % by weight of any one of the compounds A1 to A9 is divided to obtain a paste formulation for oral administration.

Formulation Example 18

Five (5) % by weight of any one of the compounds A1 to $A^9$ is mixed with 95% by weight of limestone powder, and a wet granulation method is used to obtain a granule for oral administration.

Formulation Example 19

Five (5) parts of any one of the compounds A1 to A9 are mixed with 80 parts of diethylene glycol monoethyl ether, and the mixture is mixed with 15 parts of propylene carbonate to obtain a spot-on liquid formulation.

Formulation Example 20

Ten (10) parts of any one of the compounds A1 to A9 are mixed with 70 parts of diethylene glycol monoethyl ether, and the mixture is mixed with 20 parts of 2-octyldodecanol to obtain a pour-on liquid formulation.

Formulation Example 21

To 0.5 parts of any one of the compounds A1 to A9, 60 parts of Nikkol (registered trademark) TEALS-42 (42% aqueous solution of triethanolamine lauryl sulfate, manufactured by Nikko Chemicals Co., Ltd.) and 20 parts of propylene glycol are added, and the mixture is mixed and stirred thoroughly until the solution is uniform. Then, 19.5 parts of water are added thereto, and the mixture is further mixed and stirred thoroughly to obtain a shampoo formulation as a uniform solution.

Formulation Example 22

Zero point one five (0.15)% by weight of any one of the compounds A1 to A9, 95% by weight of animal feed, and 4.85% by weight of a mixture consisting of dibasic calcium phosphate, diatomaceous earth, Aerosil (registered trademark) and carbonate (or chalk) are mixed with stirring thoroughly to obtain a premix for animal feed.

Formulation Example 23

Seven point two (7.2) g of any one of the compounds A1 to A9 and 92.8 g of Vosco (registered trademark) S-55 (manufactured by Maruishi Pharmaceutical Co., Ltd.) are mixed at 100° C., and the resulting mixture is poured into a suppository mold, followed by performing a cooling solidification to obtain a suppository.

Next, test examples are used to show an efficacy of the compound against harmful arthropods. In the following Test Examples, each test was carried out at 25° C.

Test Example 1

A test compound is made into a formulation according to the method described in Formulation Example 5, and water containing 0.03% by volume of a spreader is added thereto to prepare a diluted solution containing a predetermined concentration of the test compound.

Cucumber (*Cucumis sativus*) seedling (on the developmental stage of the second true leaf) is planted in a container and approximately 30 cotton aphids (*Aphis gossypii*) (all stages of life) are inoculated onto the leaves of the cucumber. After 1 day, the diluted solution is sprayed into the seedling in a ratio of 10 mL/seedling. Further, after 5 days, the number of the surviving insects is examined and the controlling value is calculated by the following equation.

Controlling value (%)={1−($Cb$×$Tai$)/($Cai$×$Tb$)}×100 wherein the symbols in the above equation represent the following meanings.
Cb: Number of the test insects in untreated group;
Cai: Number of the surviving insects at the time of the investigation in untreated group;
Tb: Number of the test insects in treated group;
Tai: Number of the surviving insects at the time of the investigation in treated group Here the "untreated group" represents a group where the similar treatment procedure to that of the treated group except not using the test compound is done.

The test was carried out by making the predetermined concentration 500 ppm and using the following compounds as a test compound according to the test example 1. As a result of the test, the compounds described below showed 90% or greater as the controlling value.

Compounds: A1, A2, A3, A4, A5, A6, A7, A8, A9

The test was carried out by making the predetermined concentration 200 ppm and using the following compounds as a test compound according to the test example 1. As a result of the test, the compounds described below showed 90% or greater as the controlling value.

Compounds: A1, A2, A3, A4, A5, A6, A7, A8, A9

Test Example 2

A test compound is made into a formulation according to the method described in Formulation Example 5, and water is added thereto to prepare a diluted solution containing a predetermined concentration of the test compound.

Cucumber seedling (on the developmental stage of the second true leaf) is planted in a container, and the diluted solution in the ratio of 5 mL/seedling is irrigated into the plant foot. After 7 days, approximately 30 cotton aphids (all stages of life) are inoculated onto the cucumber leaves. Further, after additional 6 days, the number of the surviving insects is examined, and the controlling value is calculated by the following equation.

Controlling value (%)={1−($Cb$×$Tai$)/($Cai$×$Tb$)}×100 wherein the symbols in the above equation represent the following meanings.
Cb: Number of the test insects in untreated group;
Cai: Number of the surviving insects at the time of the investigation in untreated group;
Tb: Number of the test insects in treated group;

Tai: Number of the surviving insects at the time of the investigation in treated group Here the "untreated group" represents a group where the similar treatment procedure to that of the treated group except not using the test compound is done.

The test was carried by making the predetermined concentration 1000 ppm and using the following compounds as a test compound according to the test example 2. As a result of the test, the compounds described below showed 90% or greater as the controlling value.

Compounds: A1, A3, A4, A5, A6, A7, A8, A9

Test Example 3

A test compound is made into a formulation according to the method described in Formulation Example 5, and water containing 0.03% by volume of a spreader is added thereto to prepare a diluted solution containing a predetermined concentration of the test compound.

Rice (*Oryza sativa*) seedling (on the developmental stage of the second true leaf) is planted in a container, and the diluted solution is sprayed into the seedling in a ratio of 10 mL/seedling. Thereafter, 20 3rd instar larvae of brown planthoppers (*Nilaparvata lugens*) are released onto the rice leaves. After 6 days, the mortality is calculated by the following equation.

Mortality rate (%)={1−the number of surviving insects/20}×100

The tests was carried out by making the predetermined concentration 500 ppm and using the following compounds as a test compound according to the test example 3. As a result of the test, the compounds described below showed 90% or greater as the controlling value.

Compounds: A1, A3, A4, A5, A6, A7, A8, A9

The tests was carried out by making the predetermined concentration 200 ppm and using the following compounds as a test compound according to the test example 3. As a result of the test, the compounds described below showed 90% or greater as the controlling value.

Compounds: A4, A5, A7, A8, A9

Test Example 4

A test compound is made into a formulation according to the method described in Formulation Example 5, and water is added thereto to prepare a diluted solution containing a predetermined concentration of the test compound.

Five (5) mL of the diluted solution described above is added to a container, and therein is installed Rice seedling (on the developmental stage of the second true leaf) that is planted in a container having a hole in the bottom. After days, 20 3rd instar larvae of brown planthoppers (*Nilaparvata lugens*) are released. After 6 days, the number of the surviving insects is examined, and the mortality is calculated by the following equation.

Mortality (%)={1−the number of surviving insects/20}×100

The test was carried out making the predetermined concentration 1,000 ppm and using the following compounds as a test compound according to the test Example 4. As a result of the test, the compounds described below showed 90% or greater as the controlling value.

Compounds: A1, A2, A3, A4, A5, A7, A8, A9

Test Example 5

A test compound is made into a formulation according to the method described in Formulation Example 5, and water is added thereto to prepare a diluted solution containing a predetermined concentration of the test compound.

In a container, 7.7 g of artificial diet (Insecta LF, manufactured by Nosan Corporation) is placed, and 2 mL of the above diluted solution is irrigated thereto. Five (5) of fourth instar larvae of tobacco cutworm (*Spodoptera litura*) are released onto the artificial diet. After 5 days, the number of surviving insects is examined, and a mortality of insects is calculated by the following equation.

Mortality (%)=(1−the number of surviving insects/5)×100

The tests was carried out by making the predetermined concentration 500 ppm and using the following compounds as a test compound according to test example 5. As a result of the test, the compounds described below showed 80% or greater as the mortality.

Compounds: A1, A4, A5, A6, A7, A8, A9

Test Example 6

A test compound is made into a formulation according to the method described in Formulation Example 5, and water containing 0.03% by volume of a spreader is added thereto to prepare a diluted solution containing a predetermined concentration of the test compound.

The diluted solution was sprayed into the cabbage (*Brassicae oleracea*) seedling (on the developmental stage of the second to third true leaf) that was planted in a container in a ratio of 20 mL/seedling. Thereafter, the stem and leaf thereof was cut out and was then installed into the container that was covered with the filter paper. Five (5) cabbage moth (*Plutella xylostella*) at the second instar larval stages were released into the cup. After 5 days, the number of the surviving insects was counted, and the mortality of insects was calculated by the following equation.

Mortality (%)=(1−the number of surviving insects/5)×100

The test was carried out by making the predetermined concentration 500 ppm and using the following compounds as a test compound according to test example 6. As a result of the test, the compounds described below showed 80% or greater as the mortality.

Compound: A1, A2, A3, A4, A5, A6, A7, A8, A9

Test Example 7

A test compound is made into a formulation according to the method described in Formulation Example 5, and water containing 0.03% by volume of a spreader is added thereto to prepare a diluted solution containing a predetermined concentration of the test compound.

The diluted solution was sprayed into the cabbage seedling (on the developmental stage of the third to fourth true leaf) that was planted in a container in a ratio of 20 mL/seedling. Thereafter, ten (10) cabbage moth (*Plutella xylostella*) at the third instar larval stages were released into the cup. After 5 days, the number of the surviving insects was counted, and the mortality of insects was calculated by the following equation.

Mortality (%)=(1−the number of surviving insects/10)×100

The tests was carried out by making the predetermined concentration 200 ppm and using the following compounds as a test compound according to test example 7. As a result of the test, the compounds described below showed 90% or greater as the mortality.

Compound: A1, A2, A3, A4, A5, A6, A7, A8, A9

Test Example 8

A test compound is dissolved into a mixed solution of polyoxyethylene sorbitan mono-cocoate and acetone (polyoxyethylene sorbitan mono-cocoate:acetone=5:95 (v/v ratio)) in a ratio of 50 μL of the mixed solution per 1 mg of the test compound. Water containing 0.03% by volume of a spreader is added thereto to prepare a diluted solution containing a predetermined concentration of the test compound.

Young seedlings of corns (Zea mays) are immersed into the diluted solution for 30 seconds. Thereafter, two of the seedling are installed in a petri dish (90 mm radius), and 10 western corn rootworms (Diabrotica virgifera virgifera) at the second instar larval stages are released onto the dish. After 5 days, the number of the died insects is counted, and the mortality of insects is calculated by the following equation.

Mortality (%)=(the number of died insects/10)×100

The test was carried out by making the predetermined concentration 500 ppm and using the following compounds as a test compound according to test example 8. As a result of the test, the compounds described below showed 80% or greater as the mortality.

Compound: A1, A4, A7, A9

Test Example 9

A test compound is made into a formulation according to the method described in Formulation Example 5, and water is added thereto to prepare a diluted solution containing a predetermined concentration of the test compound.

An inside bottom of a cup having 5.5 cm diameter is matted with a filter paper having the same diameter as that of the cup, and 0.7 mL of the above diluted solution is added dropwise to the filter paper, and then 30 mg of sucrose as a feed is placed uniformly in the cup. Ten (10) female adult houseflies (Musca domestica) are released into the cup, and the cup is sealed with a lid. After 24 hours, a life and death of houseflies is examined, and a mortality of insects is determined. The mortality of insects is calculated by the following equation.

Mortality (%)=(the number of died insects/the number of test insects)×100

The test was carried out by making the predetermined concentration 500 ppm and using the following compounds as a test compound according to test example 9. As a result of the test, the compounds described below showed 100% as the mortality.

Compound numbers: A1, A4, A5, A6, A7, A8, A9

Test Example 10

A test compound is made into a formulation according to the method described in Formulation Example 5, and water is added thereto to prepare a diluted solution containing a predetermined concentration of the test compound.

An inside bottom of a cup having 5.5 cm diameter is matted with a filter paper having the same diameter as that of the cup, and 0.7 mL of the above diluted solution is added dropwise to the filter paper, and then 30 mg of sucrose as a feed is placed uniformly in the cup. Two (2) male adult German cockroaches (Blattella germanica) are released into the cup, and the cup is sealed with a lid. After 6 days, a life and death of the German cockroaches is examined, the number of died insects is counted, and a mortality of insects is calculated by the following equation.

Mortality (%)=(the number of died insects/the number of test insects)×100

The tests was carried out by making the predetermined concentration 500 ppm and using the following compounds as a test compound according to test example 10. As a result of the test, the compounds described below showed 100% as the mortality.

Compound numbers: A1, A4, A5, A6, A7, A8, A9

Comparative Test Example 1

A test was carried out by making the predetermined concentration 500 ppm and using a compound represented by the following formula which is described in WO2017/025419 A2 (hereinafter referred to as Comparative compound 1) as a test compound according to test example 9. As a result of the test, the comparative compound 1 showed 39% or less as the mortality.

Comparative Compound 1

INDUSTRIAL APPLICABILITY

The compound of the present invention exhibits an excellent controlling effect against harmful arthropods.

The invention claimed is:
1. A compound represented by formula (I):

wherein:
$A^1$ represents CH or a nitrogen atom;
$R^1$ represents a C1-C6 alkyl group optionally having one or more halogen atoms;
$R^5$ represents $CF_3$, $C_2F_5$, or $S(O)_mCF_3$;
Q represents $NR^2C(O)OR^3$ or $N=CR^4R^6$;

R² represents a C1-C6 alkyl group optionally having one or more halogen atoms, a C3-C6 cycloalkyl group optionally having one or more halogen atoms, C(O)OR³ or a hydrogen atom;

R³ represents a C1-C6 alkyl group optionally having one or more halogen atoms, a phenyl group optionally having one or more substituents selected from Group D, or a benzyl group optionally having one or more substituents selected from Group D;

R⁴ represents a C1-C6 alkyl group optionally having one or more halogen atoms, a phenyl group optionally having one or more substituents selected from Group D, or a hydrogen atom;

R⁶ represents a C1-C6 alkyl group optionally having one or more halogen atoms, a phenyl group optionally having one or more substituents selected from Group D, or NR⁷R⁸;

R⁴ and R⁶ may combine together with a carbon atom to which R⁴ and R⁶ are attached to form a C3-C8 cycloalkylidene group;

R⁷, R⁸, R⁹ and R¹⁰ are identical to or different from each other and each represents independently a C1-C6 alkyl group optionally having one or more halogen atoms;

n is 0, 1, or 2; and m is 0, 1, or 2,

Group D: a group consisting of a C1-C6 alkyl group optionally having one or more halogen atoms, a C1-C6 alkoxy group optionally having one or more halogen atoms, a C1-C6 alkylsulfonyl group optionally having one or more halogen atoms, a nitro group, a cyano group, NR⁹R¹⁰ and a halogen atom.

2. The compound according to claim 1, wherein:
R¹ represents a methyl group; and
A¹ represents a nitrogen atom.

3. A composition for controlling a harmful arthropod comprising the compound according to claim 1 and an inert carrier.

4. A method for controlling a harmful arthropod comprising applying an effective amount of the compound according to claim 1 to the harmful arthropod or a habitat where a harmful arthropod lives.

5. A compound represented by formula (II):

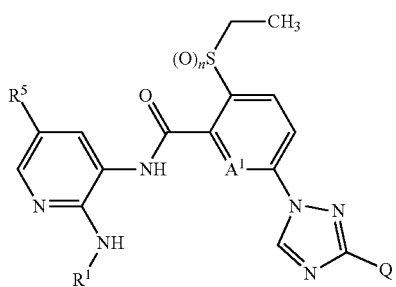

(II)

wherein:
A¹ represents CH or a nitrogen atom;
R¹ represents a C1-C6 alkyl group optionally having one or more halogen atoms;
R⁵ represents CF₃, C₂F₅, or S(O)$_m$CF₃;
Q represents NR²C(O)OR³ or N=CR⁴R⁶;
R² represents a C1-C6 alkyl group optionally having one or more halogen atoms, a C3-C6 cycloalkyl group optionally having one or more halogen atoms, C(O)OR³ or a hydrogen atom;

R³ represents a C1-C6 alkyl group optionally having one or more halogen atoms, a phenyl group optionally having one or more substituents selected from Group D, or a benzyl group optionally having one or more substituents selected from Group D;

R⁴ represents a C1-C6 alkyl group optionally having one or more halogen atoms, a phenyl group optionally having one or more substituents selected from Group D, or a hydrogen atom;

R⁶ represents a C1-C6 alkyl group optionally having one or more halogen atoms, a phenyl group optionally having one or more substituents selected from Group D, or NR⁷R⁸;

R⁴ and R⁶ may combine together with a carbon atom to which R⁴ and R⁶ are attached to form a C3-C8 cycloalkylidene group;

R⁷, R⁸, R⁹ and R¹⁰ are identical to or different from each other and each represents independently a C1-C6 alkyl group optionally having one or more halogen atoms;

n is 0, 1, or 2; and m is 0, 1, or 2,

Group D: a group consisting of a C1-C6 alkyl group optionally having one or more halogen atoms, a C1-C6 alkoxy group optionally having one or more halogen atoms, a C1-C6 alkylsulfonyl group optionally having one or more halogen atoms, a nitro group, a cyano group, NR⁹R¹⁰ and a halogen atom.

6. A method for preparing the compound represented by formula (I) according to claim 1 comprising:
a step of reacting a compound represented by formula (M1):

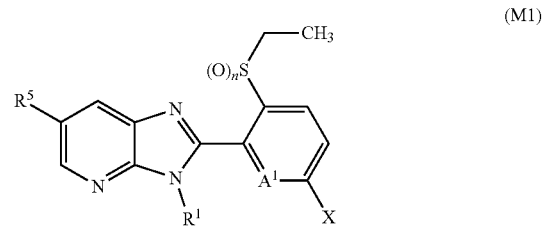

(M1)

wherein:
X represents a halogen atom;
A¹ represents CH or a nitrogen atom;
R¹ represents a C1-C6 alkyl group optionally having one or more halogen atoms;
R⁵ represents CF₃, C₂F₅, or S(O)$_m$CF₃;
n is 0, 1, or 2; and
m is 0, 1, or 2] with a compound represented by formula (M2):

(M2)

wherein:
Q represents NR²C(O)OR³ or N=CR⁴R⁶;
R² represents a C1-C6 alkyl group optionally having one or more halogen atoms, a C3-C6 cycloalkyl group optionally having one or more halogen atoms, C(O)OR³ or a hydrogen atom;

$R^3$ represents a C1-C6 alkyl group optionally having one or more halogen atoms, a phenyl group optionally having one or more substituents selected from Group D, or a benzyl group optionally having one or more substituents selected from Group D;

$R^4$ represents a C1-C6 alkyl group optionally having one or more halogen atoms, a phenyl group optionally having one or more substituents selected from Group D, or a hydrogen atom;

$R^6$ represents a C1-C6 alkyl group optionally having one or more halogen atoms, a phenyl group optionally having one or more substituents selected from Group D, or $NR^7R^8$;

$R^4$ and $R^6$ may combine together with a carbon atom to which $R^4$ and $R^6$ are attached to form a C3-C8 cycloalkylidene group; and $R^7$, $R^8$, $R^9$ and $R^{10}$ are identical to or different from each other and each represents independently a C1-C6 alkyl group optionally having one or more halogen atoms, Group D: a group consisting of a C1-C6 alkyl group optionally having one or more halogen atoms, a C1-C6 alkoxy group optionally having one or more halogen atoms, a C1-C6 alkylsulfonyl group optionally having one or more halogen atoms, a nitro group, a cyano group, $NR^9R^{10}$ and a halogen atom in the presence of a base.

7. A method for preparing the compound represented by formula (I) according to claim 1 comprising:

a step of reacting the compound represented by formula (II) according to claim 5 in the presence of an acid.

* * * * *